United States Patent
McCarthy et al.

(10) Patent No.: US 10,640,742 B2
(45) Date of Patent: May 5, 2020

(54) HYBRID LINEAR ACTUATOR CONTROLLED HYDRAULIC CELL STRETCHING

(71) Applicant: Board of Supervisors of Louisiana State University and Agricultural and Mechanical College, Baton Rouge, LA (US)

(72) Inventors: Kevin John McCarthy, Shreveport, LA (US); Deborah Jane Wassenhove-McCarthy, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 169 days.

(21) Appl. No.: 14/865,464

(22) Filed: Sep. 25, 2015

(65) Prior Publication Data

US 2016/0089673 A1  Mar. 31, 2016

Related U.S. Application Data

(60) Provisional application No. 62/055,168, filed on Sep. 25, 2014.

(51) Int. Cl.
| | | |
|---|---|---|
| C12M 1/12 | (2006.01) | |
| C12M 3/06 | (2006.01) | |
| C12M 1/00 | (2006.01) | |
| C12M 1/36 | (2006.01) | |
| C12M 1/32 | (2006.01) | |
| C12M 1/42 | (2006.01) | |

(52) U.S. Cl.
CPC ............ *C12M 23/16* (2013.01); *C12M 23/12* (2013.01); *C12M 25/04* (2013.01); *C12M 35/04* (2013.01); *C12M 41/48* (2013.01); *C12M 43/00* (2013.01); *C12M 47/00* (2013.01)

(58) Field of Classification Search
CPC ....................................................... C12M 35/04
See application file for complete search history.

(56) References Cited

U.S. PATENT DOCUMENTS

| | | | |
|---|---|---|---|
| 4,456,683 A | 6/1984 | Lintilhac et al. | |
| 4,839,280 A | 6/1989 | Banes | |
| 4,940,853 A | 7/1990 | Vandenburgh | |
| 5,217,899 A | 6/1993 | Shapiro et al. | |
| 6,037,141 A | 3/2000 | Banes | |
| 6,048,723 A * | 4/2000 | Banes | C12M 23/12 435/288.3 |
| 6,057,150 A | 5/2000 | Lee et al. | |

(Continued)

FOREIGN PATENT DOCUMENTS

| | | |
|---|---|---|
| WO | 98/19686 A1 | 5/1998 |
| WO | 00/17317 A1 | 3/2000 |

(Continued)

*Primary Examiner* — Jonathan M Hurst
(74) *Attorney, Agent, or Firm* — Davis & Bujold PLLC; Charles G. Holoubek

(57) ABSTRACT

A hydraulic cell stretching device comprising a source of variable pressured hydraulic fluid hydraulically coupled to a flexing chamber. The flexing chamber has at least one cell well. The cell well has a membrane subjected to the variable pressured hydraulic fluid.

17 Claims, 28 Drawing Sheets

(56) References Cited

U.S. PATENT DOCUMENTS

| | | | |
|---|---|---|---|
| 6,107,081 A | 8/2000 | Feeback et al. | |
| 7,906,322 B2 | 3/2011 | Bergeron et al. | |
| 8,092,491 B2 | 1/2012 | Fleischmann | |
| 2001/0021529 A1* | 9/2001 | Takagi | C12M 21/08 435/395 |
| 2003/0000965 A1* | 1/2003 | Bach | B01L 3/0206 222/135 |
| 2005/0084954 A1* | 4/2005 | Bader | C12M 35/04 435/295.1 |
| 2009/0155908 A1* | 6/2009 | Halberstadt | C12M 23/34 435/397 |
| 2010/0285558 A1* | 11/2010 | Wu | C12M 29/10 435/173.8 |
| 2012/0034695 A1* | 2/2012 | Sethu | C12M 29/18 435/401 |
| 2012/0156768 A1* | 6/2012 | Watanabe | C12M 29/14 435/289.1 |
| 2013/0109012 A1 | 5/2013 | Sniadecki et al. | |

FOREIGN PATENT DOCUMENTS

| | | |
|---|---|---|
| WO | 01/93771 A1 | 12/2001 |
| WO | 02/46364 A2 | 6/2002 |
| WO | 02/071980 A2 | 9/2002 |
| WO | 2009/032174 A1 | 3/2009 |
| WO | 2010/057672 A1 | 5/2010 |
| WO | 2011/008959 A1 | 1/2011 |
| WO | 2011/048110 A1 | 4/2011 |
| WO | 2011/103143 A1 | 8/2011 |
| WO | 2011/143294 A2 | 11/2011 |
| WO | 2012/142664 A1 | 10/2012 |
| WO | 2013/119570 A1 | 8/2013 |

\* cited by examiner

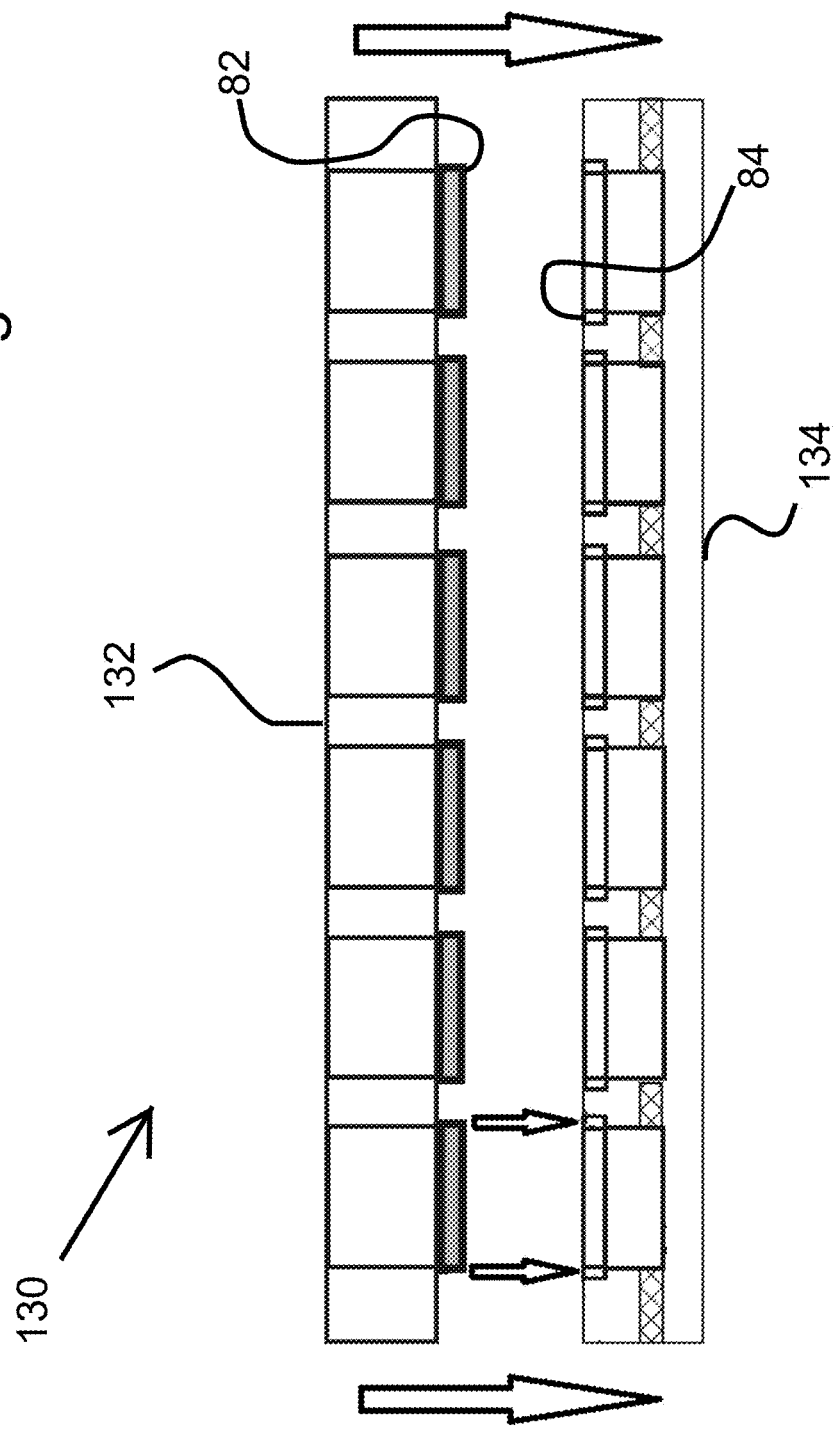

HYBRID LINEAR ACTUATOR CONTROLLED HYDRAULIC CELL STRETCHING

CROSS REFERENCE TO RELATED APPLICATIONS/PRIORITY

This invention claims priority to U.S. Provisional Patent Application No. 62/055,168 filed on Sep. 25, 2014. Provisional Patent Application No. 62/055,168 is incorporated into the present disclosure as if fully restated herein.

STATEMENT REGARDING FEDERALLY SPONSORED RESEARCH OR DEVELOPMENT

The invention was under a contract with an agency of the United States Government. The name of the U.S. Government agency is NIH/NIDDK and the Government grant/contract number is DK077860. The United States Government has certain rights in this invention.

FIELD OF THE INVENTION

The present invention relates to an electrotechnical/hydraulic cell flexing device that is capable of cyclic, high-resolution, and high gradation of stretching of a flexible membrane that carries the cell(s).

BACKGROUND OF THE INVENTION

Many cells in, inter alia, the mammalian body, including those in the circulatory system, undergo periodic flexing in vivo. Growing such cells in vitro and in a static state, results in the cells potentially responding to pharmaceuticals and other environmental stimuli in a distinct biochemical manner.

SUMMARY OF THE INVENTION

Wherefore, it is an object of the present invention to overcome the above mentioned shortcomings and drawbacks associated with the prior art.

In the disclosed cell flexing device, cells are grown under sterile conditions on a membrane that is housed in a flexing chamber. Once attached to the flexible substratum, the cells can be subjected to cyclic stretching in either direction (e.g., positive or negative stretch), mimicking the stretch-relaxation cycle of a vascular wall, for example. A first embodiment of this device is able to cycle up to at least 250 cycles per minute (4.4 Hz), which is comparable to a resting murine heart rate. The first embodiment of this device consists of a 3 well unit, each well having a flexible silicon membrane. The membrane is capable of being derivatized with a chemical cross-linker to permit the covalent coupling of ligands to the surface of the membrane. The configuration of the wells associated with the flexing chamber is such that they regulate the resting tension placed on the silicon disk. All components of the flexing chamber are preferably user-replaceable and autoclavable. Although the transmission of power from the piston stroke to the flexible membranes is best accomplished via direct hydraulic coupling, a less functional version of the unit may be designed to function via pneumatic pressure.

As will become apparent with further description below the disclosed cell flexing device has several advantages over the existing devices on the market for flexing cells in vitro. First, the disclosed cell flexing device is preferably self-contained, as regards to at least fluid force, and does not rely on an external vacuum source to provide motive force, as is common in practice today. The disclosed system can be configured to operate independent of a desktop computer controller if necessary, being configured to be controlled via an IPAD or other handheld or mobile device, with the input and the output communications maintained by direct wire connection or by radiowave (e.g. WiFi), or with integrated electrical controls, including memory, CPU, input and output. The disclosed cell flexing device will also preferably incorporate a battery-backup system to permit an end user to maintain the cell stretching activity of the device during power outages or while moving the device within the laboratory environment. This allows the user to perform month(s) or year(s) long continuous experiments without out stopping the cell stretching activity of the device.

Second, a fluid coupling of the piston to the flexible membranes permits precise application of a wide range and fine gradation of user controllable strain, currently unavailable in the art. The captive hybrid linear actuator drive is powerful, reliable, and capable of prolonged uninterruptible duty cycles. The first disclosed embodiment has functioned for over a year of continuous operation. For this embodiment, the resolution of the actuator is at 63 μm per step, and the final membrane displacement of the flexible membrane in the well is a function of the actuator lead screw/rod stroke and the piston area relative to the total membrane area. Depending on the intended application of the device, these parameters can be easily manipulated/altered by one of ordinary skill in the art by changing the design or function of the linear actuator and/or by modifying the dimensions of the cylinder/piston assembly. During the flexing regimen, the movement (amplitude and frequency) of the linear actuator, and thus the membrane is regulated by user-defined commands set up in the software.

Third, unlike existing devices on the market, the linear actuator system can run a single step stretch (i.e. from point A to point B) and hold at that position for a preset period of time. This allows for the direct in vivo imaging of biosensor activation in response to a single displacement force.

Fourth, the substrate is easily derivatizable silicon, which permits coupling a wide range of ligands to the substratum for cell adhesion.

Fifth, the production cost of the hydraulic cell flexing device is very economical. The first embodiment materials cost is less than $800/unit. The hydraulic cell flexing device is also scalable from the one to three wells in the first embodiment. Well plates ranging from, for example, a single well, to 12 wells to at least 384 wells are possible, allowing the system to be used in high throughput screening assays.

Sixth, unlike existing devices, this hydraulic cell flexing device is capable of multiplex flexing within the same apparatus. That is, the rate and degree of flexing between multiple groups or rows of flexing wells can be differentially regulated. This can be accomplished via the incorporation of multiple drive modules in a single apparatus, or the incorporation of multiple pressure limiting valves/pressure regulators for a single or multiple drive module(s). Using the multiple drive module approach, multiple flexing regimens to be applied to different groups of cells during the same experiment period on the same apparatus, with the reliability and fine control offered by separate drive modules for each hydraulic pressure line. Using the multiple pressure regulator approach, multiple flexing regimens to be applied to different groups of cells during the same experiment period on the same apparatus may also be achieved, with multiple pressure lines from a single drive module, and a pressure regulator on most, or all, or all but one pressure line. Each of these approaches will save users both the cost of materials and experimentation time, and dramatically increases the functionality available to users.

The present invention also relates to a hydraulic cell stretching device comprising a source of variable pressured hydraulic fluid hydraulicly coupled to a flexing chamber, the flexing chamber having at least one cell well, and the cell well having a membrane subjected to the variable pressured hydraulic fluid.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIG. 28 is a schematic drawing of the upper plate of FIGS. 24 and 25 mating with the lower plate of FIGS. 26 and 27.

DETAILED DESCRIPTION OF THE PREFERRED EMBODIMENTS

The present invention will be understood by reference to the following detailed description, which should be read in conjunction with the appended drawings. It is to be appreciated that the following detailed description of various embodiments is by way of example only and is not meant to limit, in any way, the scope of the present invention.

Figure 1:
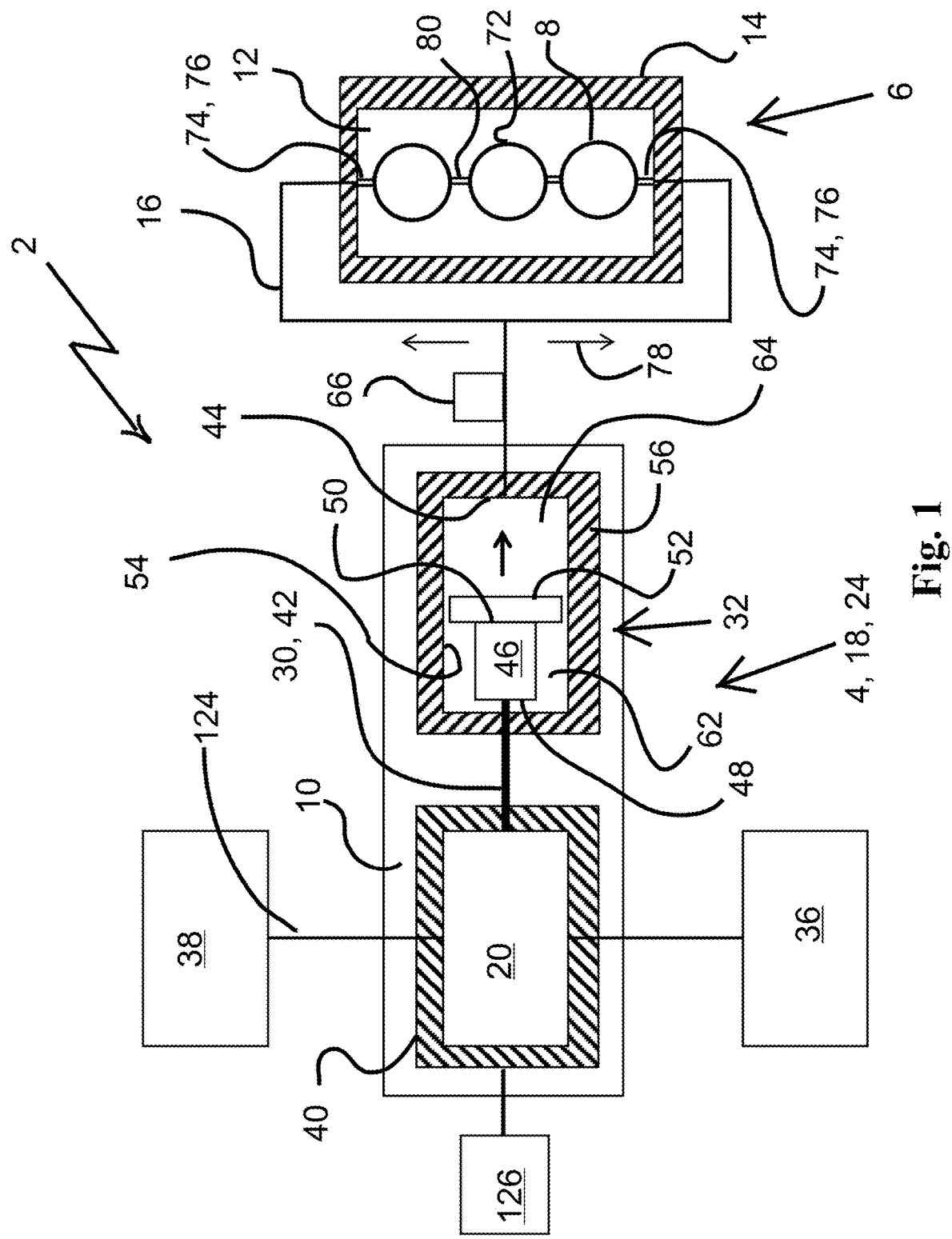
FIG. 1 is a diagrammatic top view of a first embodiment of the hydraulic cell flexing device with the piston conducting a high pressure stroke.

Turning now to FIG. 1, a brief description concerning the various components of the present invention will now be briefly discussed. As can be seen in this embodiment, the hydraulic cell flexing device 2 is comprised of a source of variable pressured hydraulic fluid 4 and a flexing chamber 6 comprising one or more cell wells 8. The source of variable pressured hydraulic fluid 4 and the flexing chamber 6 are both preferably mounted on a single foundation plate 10.

FOUNDATION PLATE—In the embodiment shown a foundation plate 10 measures approximately 11.5"×3"×0.5", though this can vary based on the spacing of the constituent parts of the hydraulic cell flexing device 2. The foundation plate 10 will preferably provide enough surface area to mount the constituent parts of the hydraulic cell flexing device 2 thereupon, with little extra overhang. The foundation plate 10 is made of polycarbonate, being relatively transparent, rigid, and chemically inert, but may alternatively be made of another plastic or metal, for example, such as aluminum alloy.

The one or more cell wells 8 of the flexing chamber 6 are preferably mounted in a flexing chamber baseplate 12, which may attached to foundation plate 10, or as shown in FIG. 1, mounted on a separate flexing chamber mounting 14, offering, inter glia, greater flexibility of positioning. Alternatively, the baseplate 12 may function as the flexing chamber mounting 14 also. The fluidic connection 16 between the flexing chamber 6 and the source of variable pressured hydraulic fluid 4 in this case is established via semi-rigid plastic tubing 16 (described further below), approximately ⅛" internal diameter ("ID"). The ID wall thickness of the tubing 16 can preferably range from 1/64" to ½", and more preferably from 1/32" and ¼".

Figure 12:
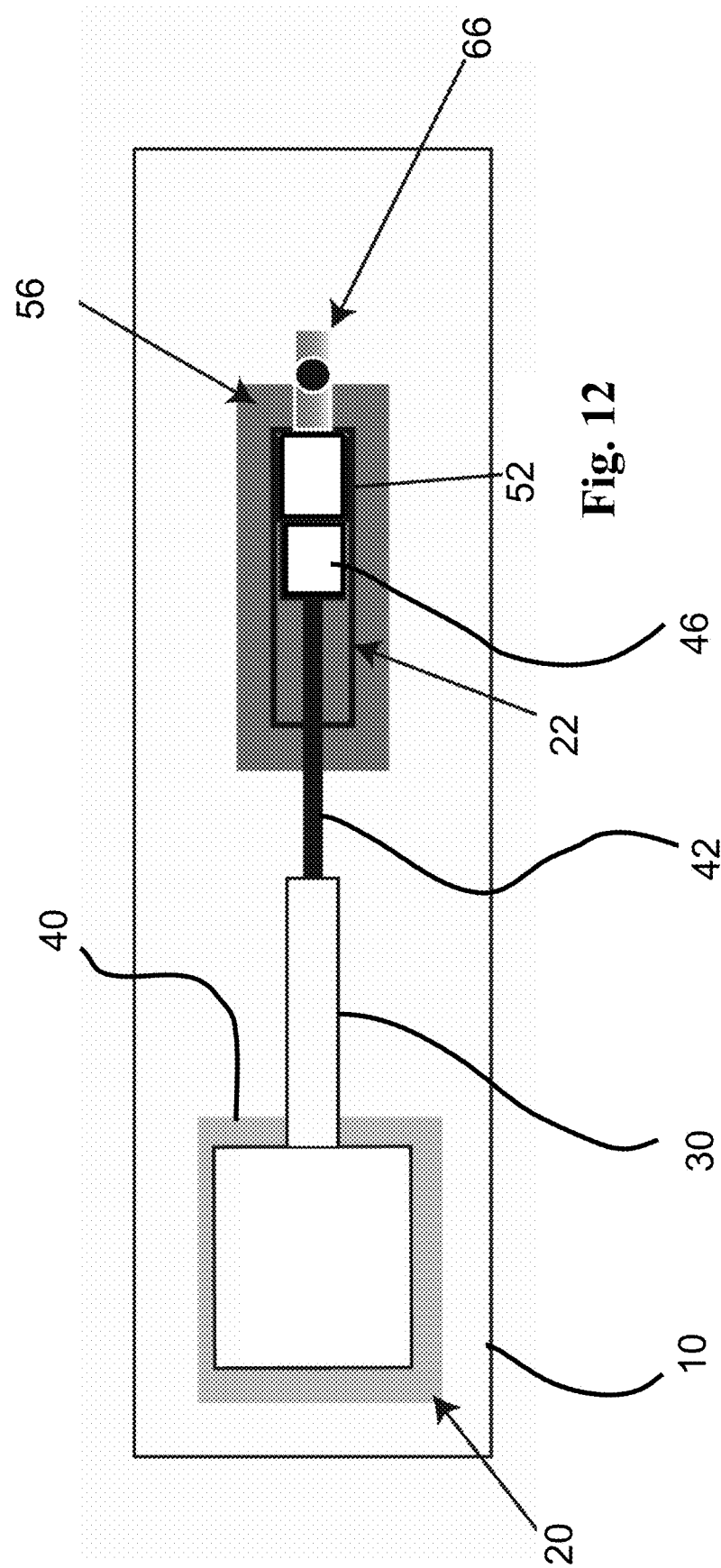
FIG. 12 is a diagrammatic top view of the drive module of FIG. 1.
Figure 13:
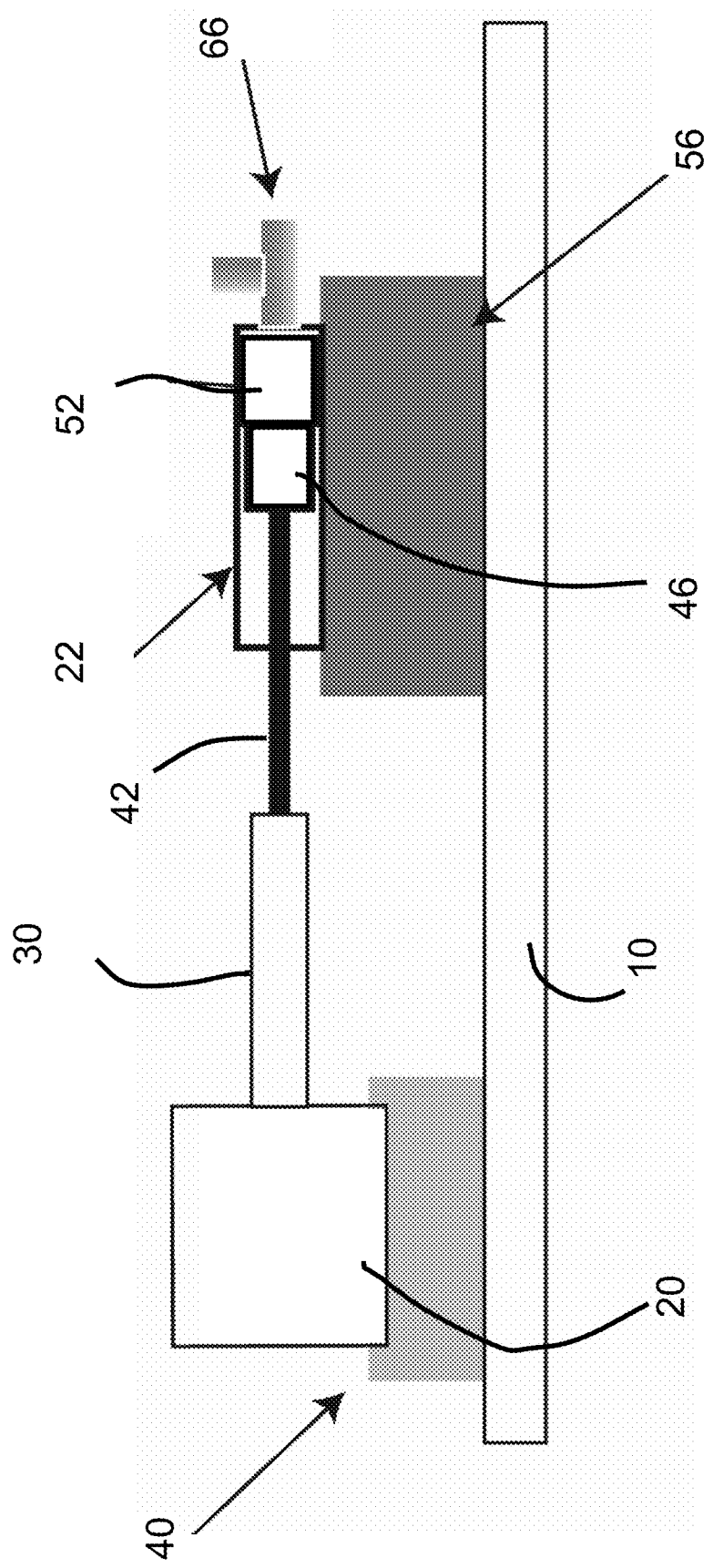
FIG. 13 is a diagrammatic side view of the drive module of FIG. 1.

VHPF—In the embodiment shown in FIGS. 1, 12, and 13, the source of variable pressured hydraulic fluid 4 is a reciprocating hydraulic piston 18 comprised of a computer interfaced captive hybrid linear actuator 20 coupled to a piston and cylinder assembly 22—the combined actuator 20 and piston/cylinder assembly 22 may be referred to as a drive module 24 for the hydraulic cell flexing device 2.

ACTUATOR—The hybrid linear actuator 20 is an electro-mechanical actuator 26, where the actuator 26 is powered by a stepper motor 28 such as the commercially available hybrid double stack stepper motor linear actuators from Hayden Kerk Motion Solutions sold under the trade name Idea™ Drive. The stepper motor 28 allows very fine gradations of linear travel of the actuator rod 30 per step. This, in turn, as described below, allows very fine control of piston 32 actuation, very fine control of fluid pressure, and in turn very fine control of cell well membrane 34 flexing.

A linear encoder 36, having a sensor, transducer or readhead paired with a scale that encodes position, is preferably included in the device 2. The linear encoder 36 allows detailed feedback to the computer controller 38/software with regard to precise positioning of the actuator rod 30/piston 32 assembly, the length/speed of strokes and the number of strokes per minute.

The linear actuator 20 in the embodiment shown is mounted on an actuator mounting 40 of two blocks of pure polycarbonate, each reinforced with two aluminum bars. The aluminum bars reinforce the base of the mounting system 40 to resist any flexing due to the motion of the actuator 20. The linear actuator mounting 40 could alternatively be one or more blocks of metal free polymer, or of one or more blocks of pure metal, such as a cast aluminum chassis. A solid, honeycombed, or webbed pure metal mounting 40 could provide both additional strength and increased dissipation of heat generated by the drive module 24.

The hybrid linear actuator rod 30 extends from the actuator motor 28 towards the piston 32, and is attached to the piston 32 of the piston and cylinder assembly 22. The actuator rod 30 functions as the piston rod 42, pushing and pulling the piston 32 with each linear stroke of the actuator rod 30.

PISTON—The piston and cylinder assembly 22 is comprised of a cylinder 44 and a piston 32, both axially aligned with the rod 30 of the hybrid linear actuator 20. The piston 32 in the embodiment shown is made of a first, preferably polycarbonate ("PC"), piston portion 46 having a first diameter and being attached to the actuator rod 30 on a first axial side 48 of the first/PC piston portion 46. The PC piston portion 46, on its second axial side 50, is bonded to a second polytetrafluoroethylene ("PTFE") piston portion 52 having a second diameter. The second diameter is preferably larger than the first diameter. The PC and PTFE piston portions 46, 48 are cemented to one another using, for example, cyanoacrylate cement. The PC piston portion 46 provides strength and support for the PTFE piston portion 48. The PTFE piston portion 48 is machined to tightly fit within the bore 54 of the cylinder 44 allowing for a leak-resistant seal and yet permit movement of the piston 32 within the cylinder 44. Alternatively, the piston 32 may be made of a single piston portion 46, and one or more elastomeric or metal piston seals may be provided along an exterior circumference of the piston 32.

CYLINDER—The cylinder 44 is made of PC and is sized to retain the piston 32, allowing movement within the cylinder 44 with a leak-resistant seal. The PC cylinder 44 is cemented to a cylinder mounting block 56. The cylinder 44 is aligned to the piston 32 during assembly 22 of the device 2 via mounting screws through the bottom of the foundation plate 10 to the underside of the cylinder mounting block 56.

The parameters of the hydraulic linear actuator 20 and the dimensions of the piston/cylinder assembly 22 are not set parameters. In subsequent embodiments the parameters and dimensions may vary based on application. The pumping action of the drive module 24 in this embodiment is derived from a series of variable factors: 1) the motor 28 design (stepper/single or double stack); 2) the configuration of the lead screw (e.g. number of threads per inch); and 3) the final dimensions of the piston cylinder assembly 22 (e.g. changing the circumference of the piston 32/cylinder 44 would change, in a direct coloration, the displacement of hydraulic fluid per stroke).

Figure 17:
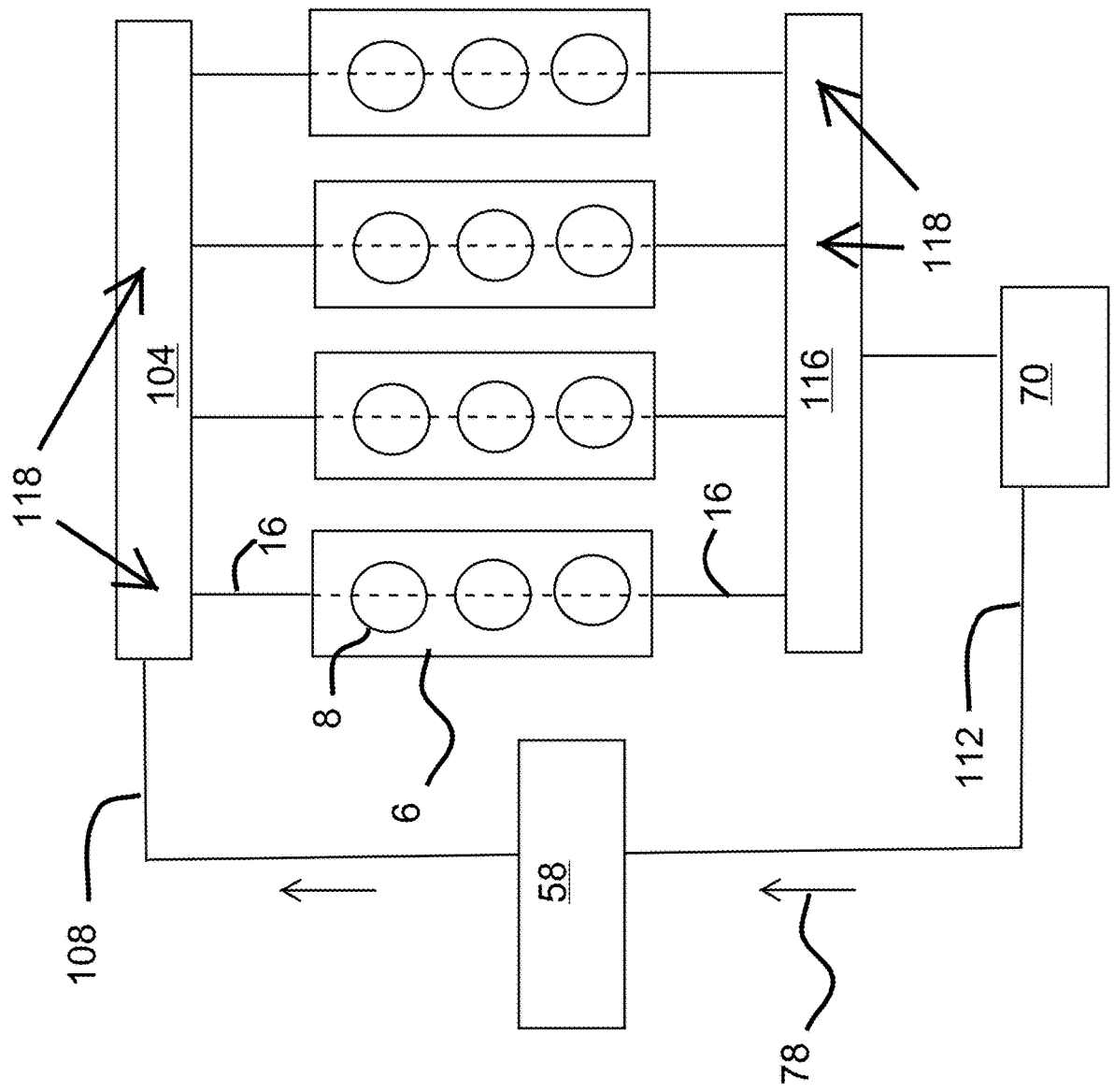
FIG. 17 is a hydraulic circuit of a continuous pressure source hydraulic cell flexing device.

Although the first embodiment discloses a hybrid linear actuator 20/piston cylinder assembly 22 drive module 24 as a source of variable hydraulic pressure 4, other embodiments are envisioned. For example, as shown in FIG. 17, a hydraulic pump 58 which delivers a continuous hydraulic pressure, or a pressure that was continuously maintained above a specific lower limit, within a closed loop circuit with the output/pulsatile force from the closed loop system being delivered to the flexing chamber 6 baseplate 12 assembly via a set of computer actuated hydraulic valves 60, such as output control valves 60 between the wells 8 and a sump 70 to allow pressure build up when the valves 60 are closed and controlled release to the sump 70 when the valves 60 are open; multi-port valves 60 between the pump 58 and the separate pressure lines 16 to deliver pressure from a single source to separate lines 16; and input control and regulator valves 60 or both along each pressure line 16 between the multi-port valves 60 and the wells 8 to deliver different hydraulic pressure to different lines 16 from a single pressure single source. The input control valves 60 would open, and the output control valve 60 would close, allowing regulated pressurized hydraulic fluid 68 to flex the membrane 34 for a given time. Then the input control valves 60 would close and the output control valves 60 would open, dumping the pressurized fluid 68 into the sump 70, and allowing the flexible membrane 34 to relax.

Another drive module 24 envisioned is an onboard, self-contained microfluidic drive module 24 for the single cell flexing device 2 that would provide actuation for one single well 8 in the baseplate 12.

STOPCOCK & PRESSURE LINE—In the embodiment shown, the rod 42 extends into the cylinder 44 on a first axial end 62 of the cylinder 44. On the second axial end 64 of the cylinder 44, containing pressurized fluid space, an optional bleeding valve 66, such as a stopcock, connects the cylinder 44 to a pressure line 16. The bleeding valve 66 preferably has multiple ports, e.g. a 3 or 4 way stopcock. The function of the stopcock is to fill the system with the hydraulic fluid 68 and to assist with purging from the system prior to operation. The shown embodiment uses water as the hydraulic fluid 68. Other valves 66 are anticipated being used. Alternatively, the pressure line 16 could be connected directly to the cylinder 44.

The pressure line 16 is a chemical resistant flexible tubing 16, preferably Tygon™ type, that is attached to standard fluidic fittings (preferably a Luer Taper connection such as a Luer-Lock or Luer-Slip) mounted on the baseplate 12 and incorporated into the 4 way stopcock. Because transfer of force derived from the piston 32 stroke is via a hydraulic coupling, the system 2 is less prone to loss of force over distance. The efficiency of the of the system 2 can be enhanced via incorporation of rigid wall tubing 16 elements rather than the more flexible Tygon™ tubing 16, but with the potential tradeoff of cost and less adjustability. The pressure line 16 functions to carry the pressurized fluid 68 from the cylinder 44 to the one or more wells 8 in a flexing chamber 6.

WELLS—In the embodiment shown in FIGS. 1-9, three wells 8 are arranged in a single row in a flexing chamber 6. The flexing chamber 6 is comprised of a baseplate 12 having boreholes 72 drilled within, cell wells 8 mounted in the boreholes 72, and at least one pressure inlet 74 and preferably at least one pressure outlet 76. In the hydraulic circuit depicted in the embodiment of FIG. 1, both hydraulic openings 74, 76 in the baseplate 12 function as both pressure inlets 74 and pressure outlet 76, depending on the stroke direction of the piston 32. When the piston 32 is performing a high pressure stroke, as depicted in FIG. 1, both hydraulic openings 74, 76 in the baseplate 12 function as both pressure inlets 74. The flow arrows 78 showing the direction of fluid 68/pressure flow. Alternatively, when the piston 32 is performing a low pressure stroke, or in the opposite direction as depicted in FIG. 1, that is, to the left of the FIG., the fluid 68/pressure flow would be reversed and both hydraulic openings 74, 76 in the baseplate 12 would function as pressure outlets 76. A hydraulic bore 80 fluidly connects the boreholes 72 to each other and to the hydraulic openings 74, 76 to allow the hydraulic fluid to pass from the pressure inlets 74 through the hydraulic bore 80 to the cell wells and then through another hydraulic bore 80 and out via the pressure outlets 76.

The baseplate 12 in the first embodiment is constructed/machined from virgin polycarbonate sheet. PC material is durable, resists pressure, and is capable of being sterilized by autoclave. The baseplate 12 could also be made via injection-molding of polycarbonate or by 3D printing using a plastic resin that is conducive for cell culture conditions (e.g. FDA approved for use in live tissues).

Figure 2:
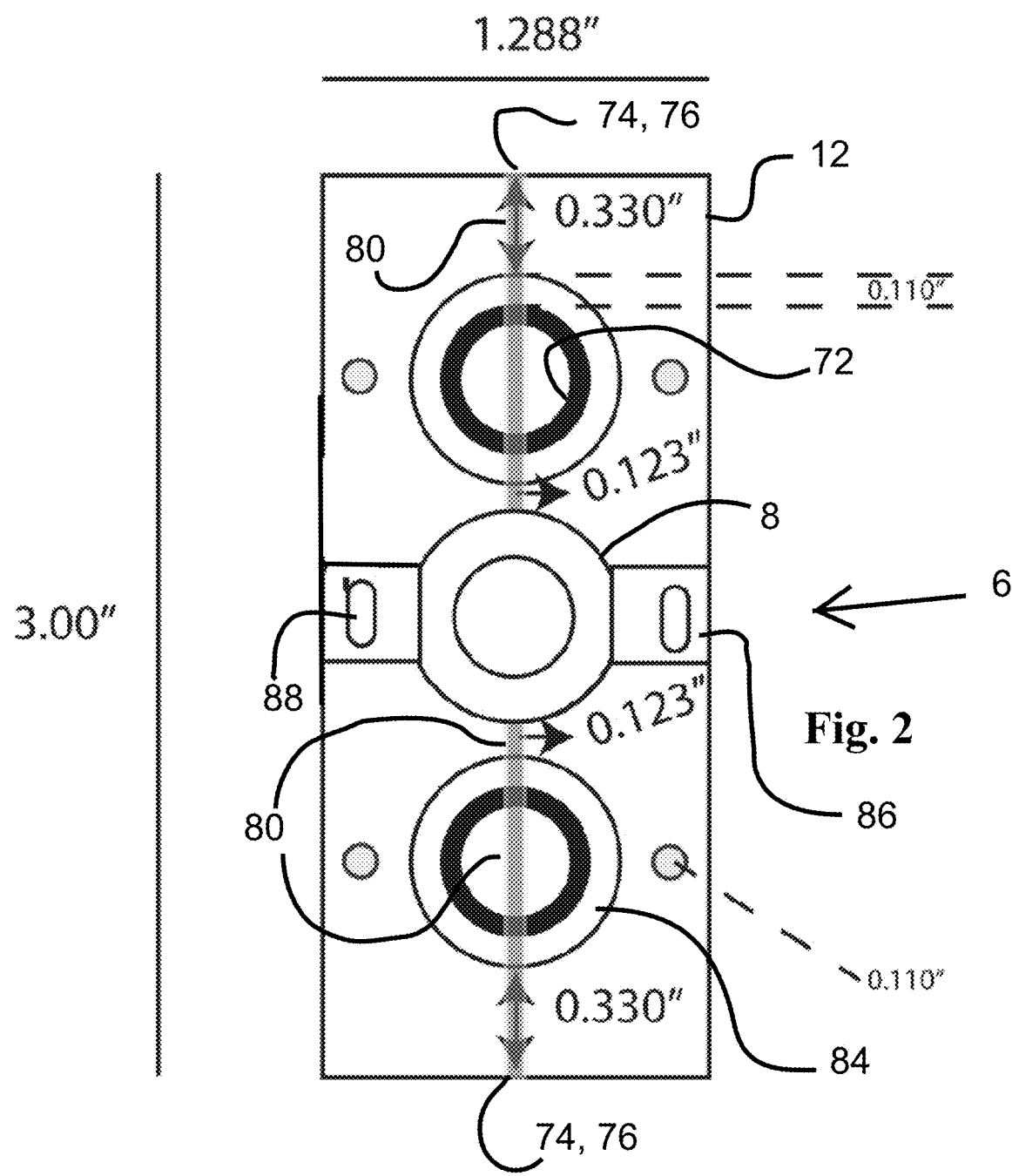
FIG. 2 is a diagrammatic top view of the base plate of FIG. 1.
Figure 3:
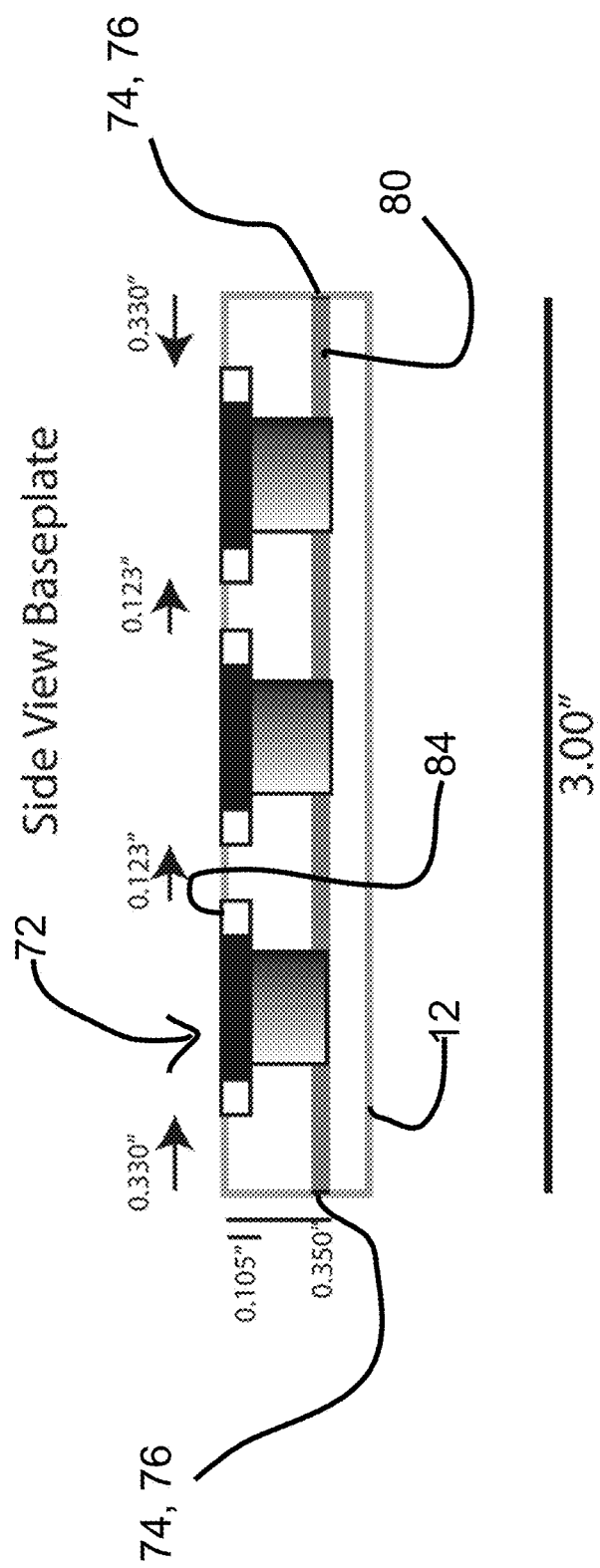
FIG. 3 is a diagrammatic side view of the baseplate plate of FIG. 1.
Figure 4:
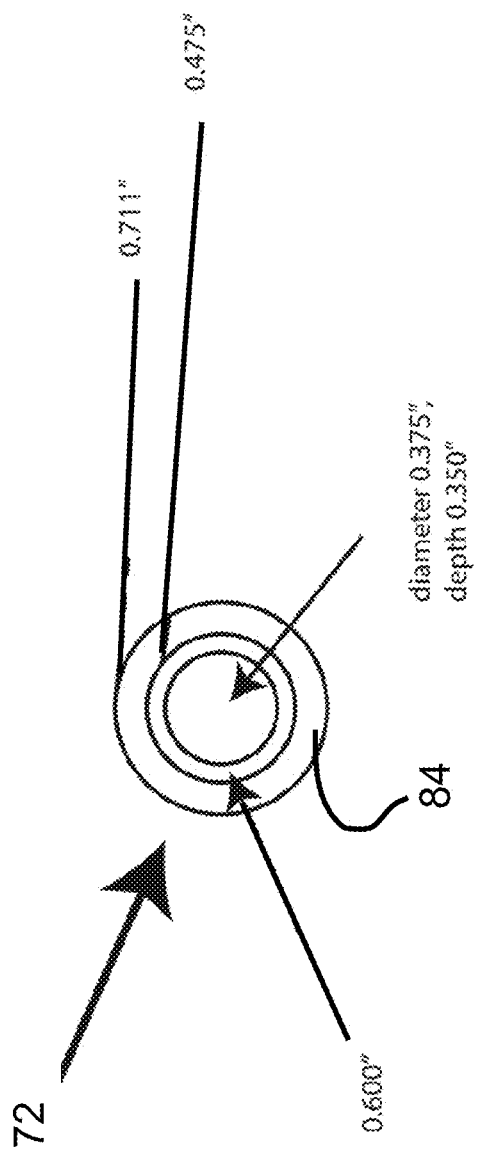
FIG. 4 is diagrammatic top view of the bottom well bore of the baseplate of FIG. 1.
Figure 5:
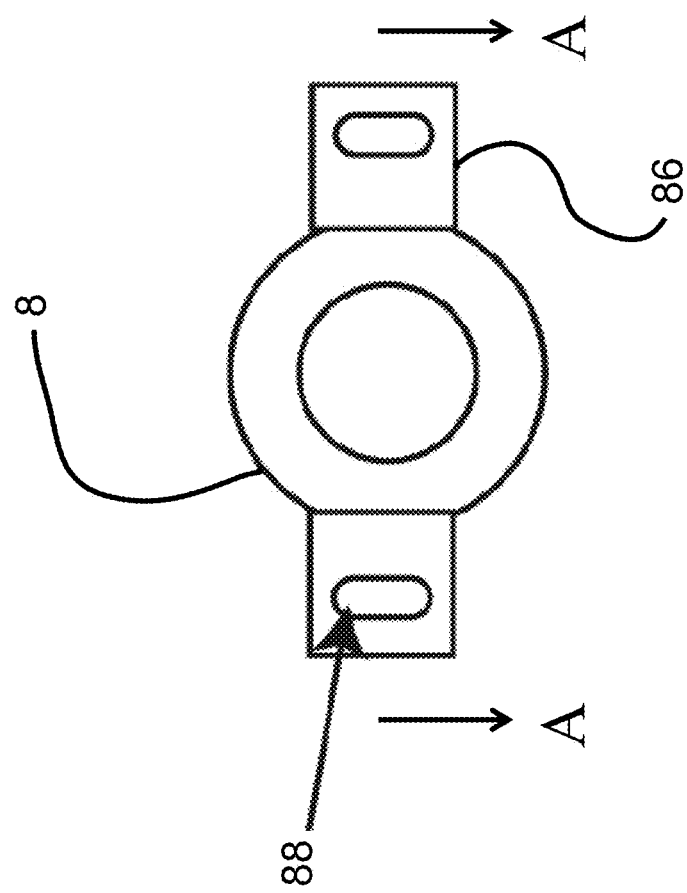
FIG. 5 is a diagrammatic top view of the cell well in the middle well bore of FIG. 1.
Figure 6:
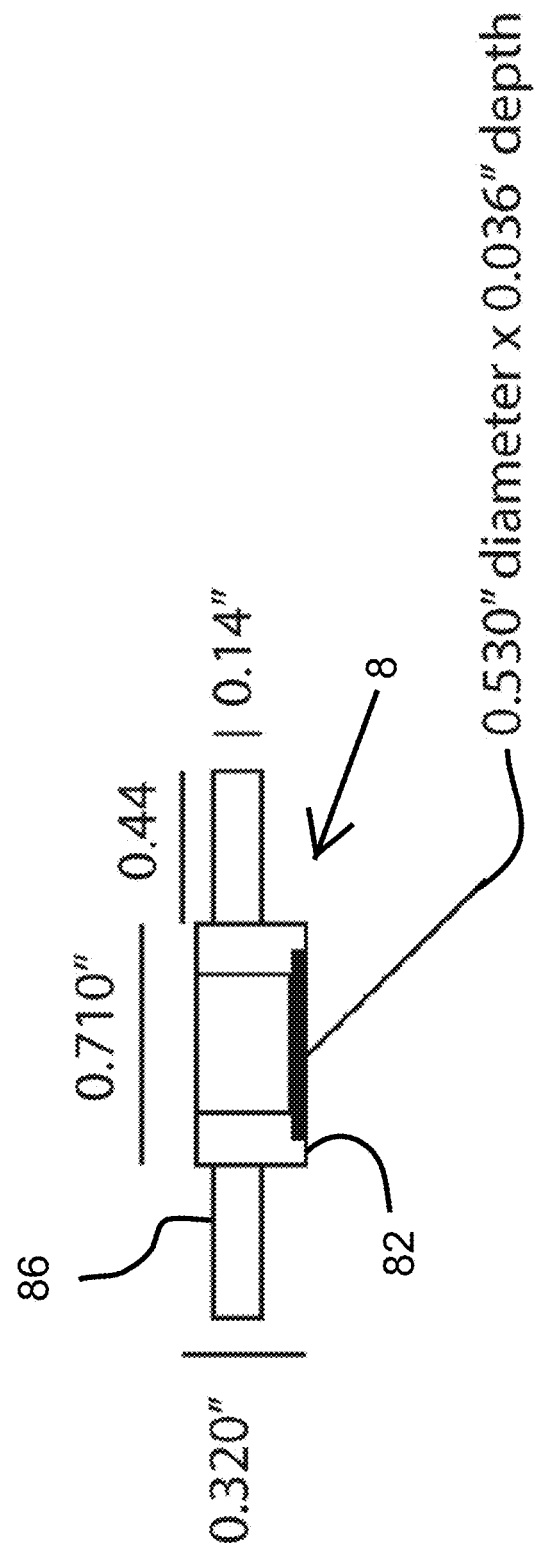
FIG. 6 is a lateral sectional view of the cell well of FIG. 5 in the direction of arrows A.
Figure 7:
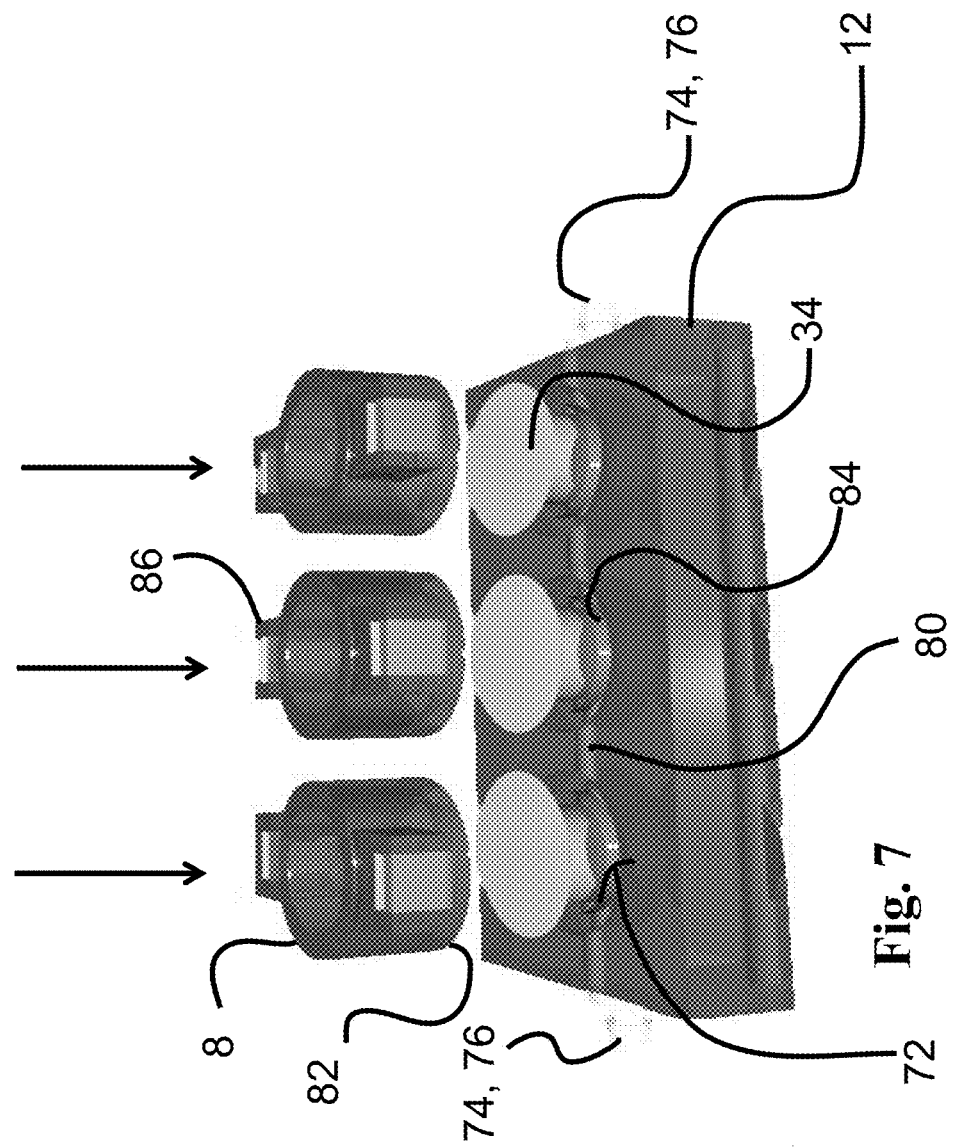
FIG. 7 is an exploded isomeric view of a flexing chamber similar to the one shown in FIG. 1.

Turning to FIG. 2, a line drawing of the dimensions of the 3 well baseplate 12 of FIG. 1 is shown. The radius of baseplate 12 mounting points for the cell wells 8 are cut into the baseplate 12 using a specially constructed radial boring tool using a bench top milling apparatus. The dimensions for the diameter of the mounting points, the distance between each mounting point are shown in the drawing. A hydraulic bore 80 with an input 74 and preferably an output 76 is formed transversely in the baseplate 12, with a portion of the hydraulic bore 80 running through a bottom portion of each cell well borehole 72. The hydraulic bore 80 can be a linear bore, as shown in FIGS. 2 and 7 for example, where the input and output are aligned with the cell well bores. Alternatively, the hydraulic bore can be a "T" shaped bore, where a first through section of the hydraulic bore 80 extends from the input and the output beneath the central cell well and orthogonal to the cell well's 8 alignment. The first section of the hydraulic bore 80 intersects a second section of the hydraulic bore 80 the connects and is aligned with the remaining cell wells 8. However, hydraulic bore embodiments of FIGS. 2 and 7 are preferred, as there are not any hydraulic dead ends, as is created in each axial end of the second section T shaped hydraulic bore 80 embodiment.

The cell wells 8 were also constructed from polycarbonate stock and were turned to size as cylindrical blanks (see dimensions on FIGS. 2-6) using a bench top lathe. The center hole was bored in each blank using a drill bit, with the final opening diameter cut using a boring tool. After boring, the cylindrical blanks were cut into smaller cylinders (0.32"), the base of each smaller cylinder further machined on the lathe to give an inset 82 (see dimensions FIGS. 2-6). This inset 82 serves at least two functions: 1.) the inset 82 orients the cell well 8 correctly to the mounting point 84 on the baseplate 12; 2.) the inset 82 serves as part of a tensioning system of the silicon membrane disc 34 (see FIGS. 7-9) that is mounted to the bottom of the cell well 8. The latter tensioning system particularly helps to maintain the tautness of the silicon disc 34 within the cell well 8. The outer walls of the cell well 8 are further machined to accept attachment (via cement in the embodiment shown) of mounting tabs 86. The mounting tabs 86 serve at least two functions: 1.) the mounting tabs 86 serve to firmly anchor the cell well 8 to the baseplate 12 via screws that are placed through slots 88 in the mounting tabs 86 into the baseplate 12; 2.) the mounting tabs 86, via the torque placed upon the anchoring screws, serve as part of the silicon disc 34 tensioning system. Although this section describes the methods used to build/machine the first embodiment, other embodiments can be easily produced at minimal cost using injection molding or 3D printing.

Turning now to FIG. 7, an exploded isometric drawing shows a pictorial description of the version of the flexing chamber 6 of the first embodiment. Each well 8 (black arrows) is capable of being independently fastened to the baseplate 12 via set screws (not illustrated) that engage the mounting tabs 86/lateral ears on the wells 8. In further embodiments, the fastening system may changed. For example, in large scale manufacturing of the baseplate 12 assembly, the cell wells 8 could be machined/molded as a single piece, as with the baseplate 12. The silicon membrane 34 would be cemented in place between the cell well 8 upper plate and the lower baseplate 12. A version of this further embodiment is described with reference to FIGS. 23-27 below.

Figure 8:
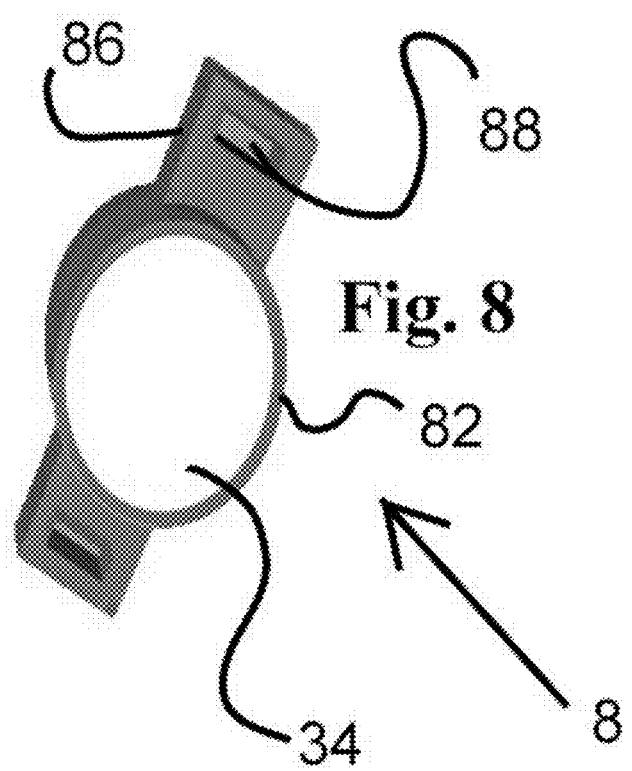
FIG. 8 is bottom isomeric view of one of the cell wells of FIG. 1.
Figure 9:
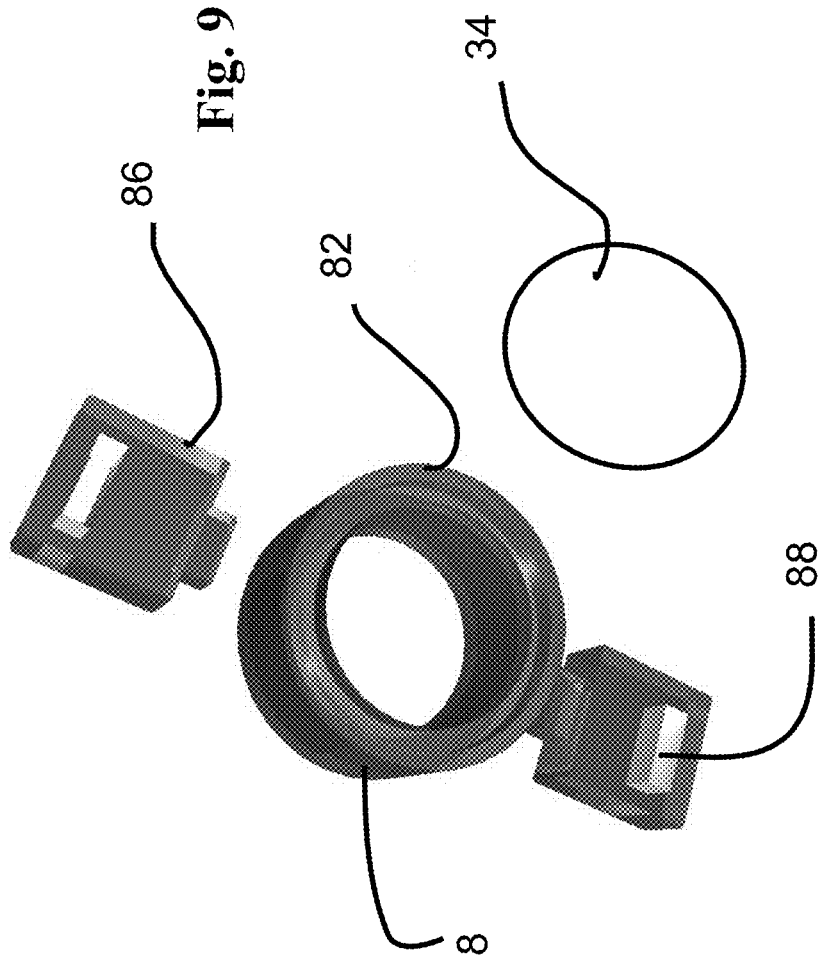
FIG. 9 is an exploded isomeric view of the cell well of FIG. 8.

As shown in FIGS. 7-9, the cell well 8 consists of a silicone membrane pad 34 (white in adjacent FIG. 8) that is preferably bonded (via adhesive or by laser bonding) to the outer lip of the cylinder adjacent to the inset 82. As described above, the inset 82 in the lower surface of the cell well 8 (see FIG. 9) has at least two functions: 1) docking the cell well 8 to the respective machined lip or mounting point 84 present in the baseplate 12, which assists in developing a fluid-tight seal to the baseplate 12; and 2) providing a circumferential pressure around the perimeter of the silicon disk, regulating the overall tension of the silicon substrate. By regulating the depth of the inset 82 in the lower surface during the manufacturing process, the tension of the silicon disc can be precisely and repeatedly controlled. In addition, changing the diameter and depth of the inset 82 during manufacturing also allows for the use of flexible silicon disks 34 of different thicknesses.

Figure 18:
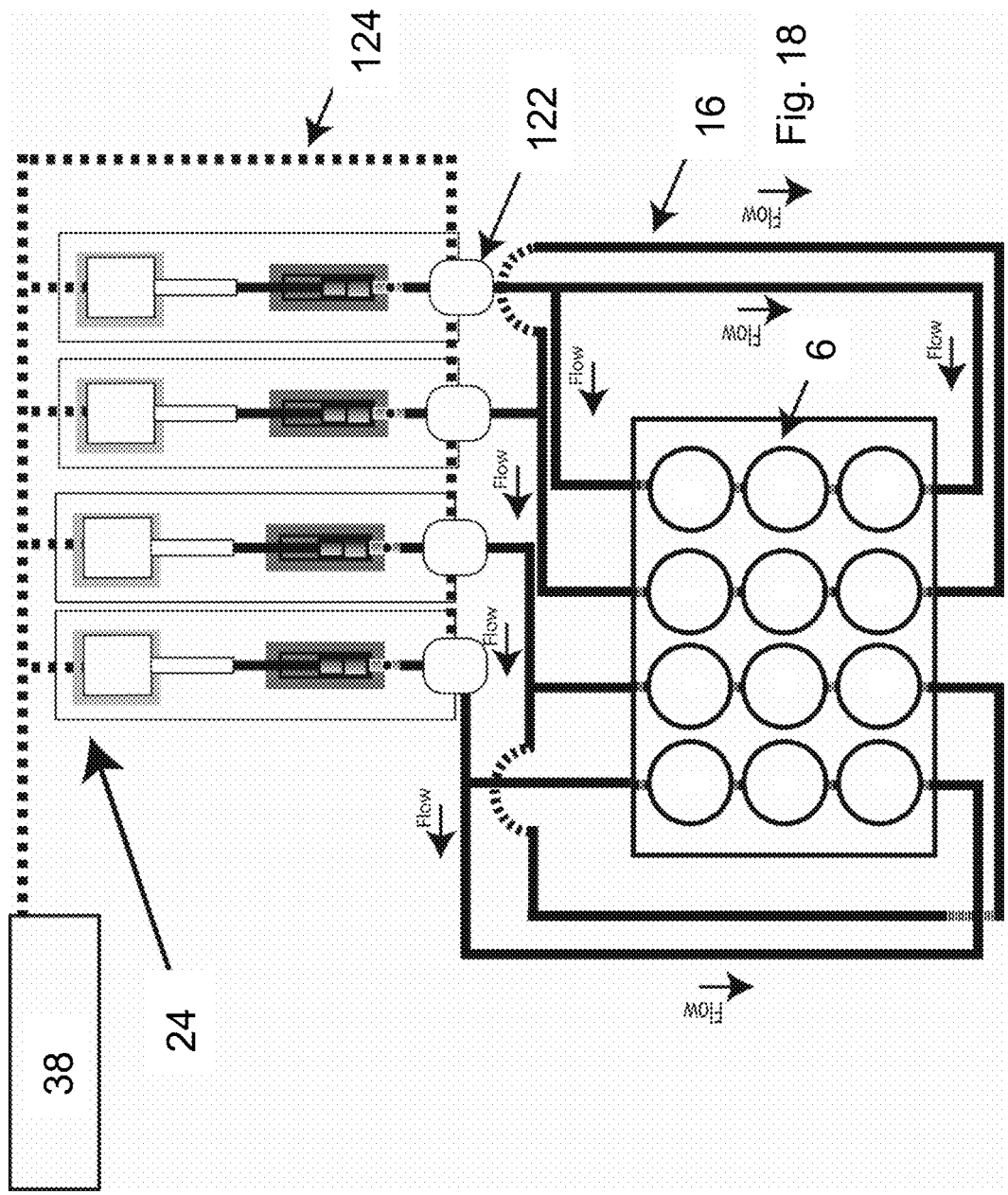
FIG. 18 is a schematic drawing of a hydraulic cell flexing device with multiple drive modules, each coupled to a respective row of wells.

While the first embodiment baseplate 12 consists of 3 functional wells 8, alternative arrangements are possible. A 12 well 8 system is also preferred, as it would allow three wells 8 each for three variables and a control. As shown in FIG. 18, the 12 well 8 system would be based on the first embodiment, but with the baseplate 12 consisting of 4 rows of 3 wells 8 each. The wells 8 in each row are coupled via hydraulic bores/channels bored in the baseplate 12, comparable to the first embodiment, with each row having a separate hydraulic input and output. Each row, however, is hydraulically isolated from adjacent rows. The hydraulic isolation serves to allow for differential flexing of individual rows of cell wells 8 within a baseplate 12 via, for example, "multiplexing" of separate drive modules 24. The hydraulic isolation also allows the incorporation of "non-flexing" rows of wells 8 in the same baseplate 12 to serve as internal controls during experimentation. For example, this allows testing for the differential effects of flexed versus non-flexed cells under identical conditions.

Figure 16:
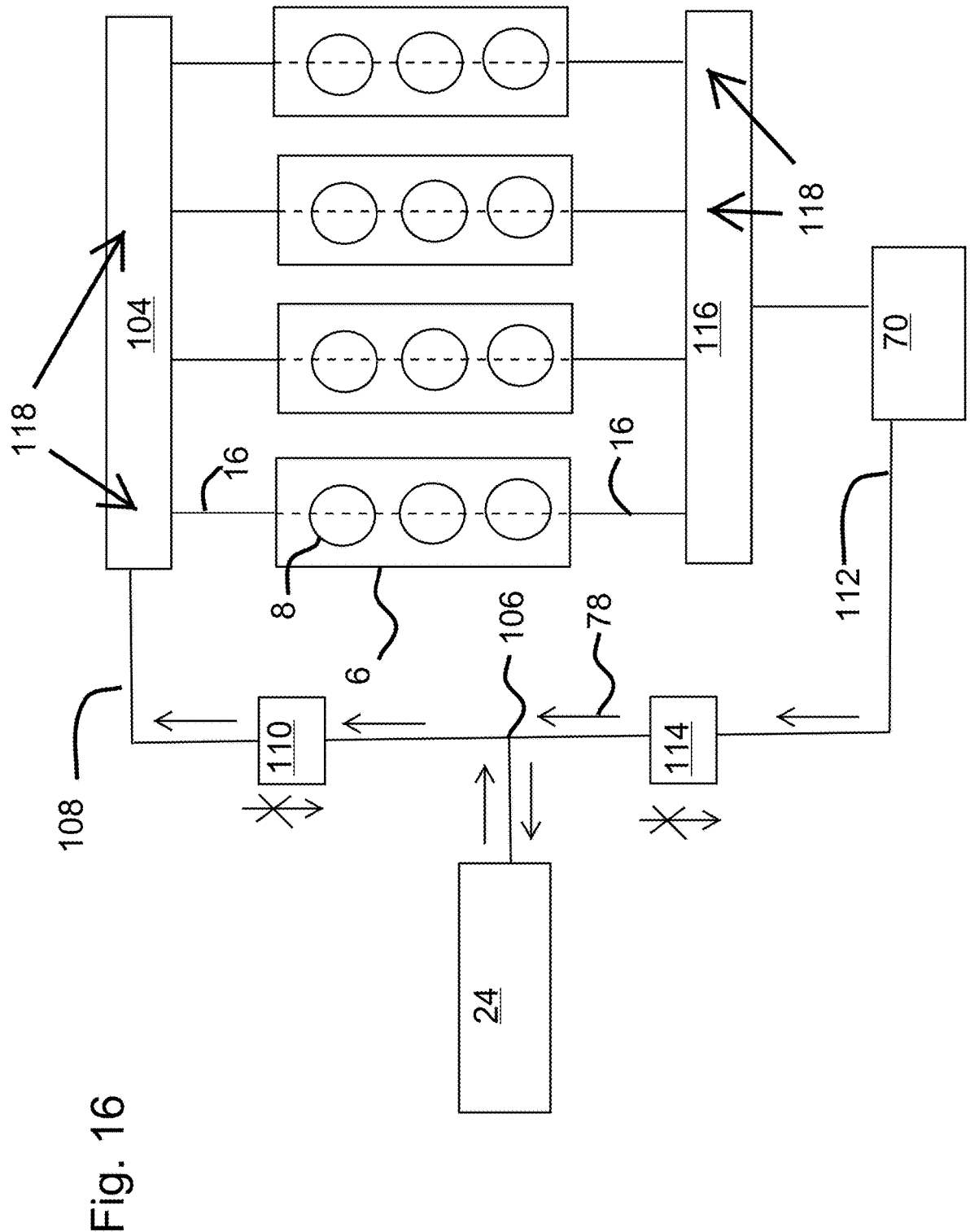
FIG. 16 is a hydraulic circuit of a single drive module multiple pressure line hydraulic cell flexing device.

Continuing, FIG. 18 shows the multiplex capability (multiple rows of wells 8 within a baseplate 12) could be actuated at different parameters (rates, degree of stretch) within a baseplate 12 using a combination of several drive modules 24, all interfaced to the same computer 38 interface. Alternatively, as shown in FIG. 16, one drive module 24 could be used, and multiple pressure lines 16 could run from the one drive module 24, with the different pressure lines 16 regulated by regulator valves 60 set to different pressure maximums to allow for different degrees of stretch.

Figure 10:
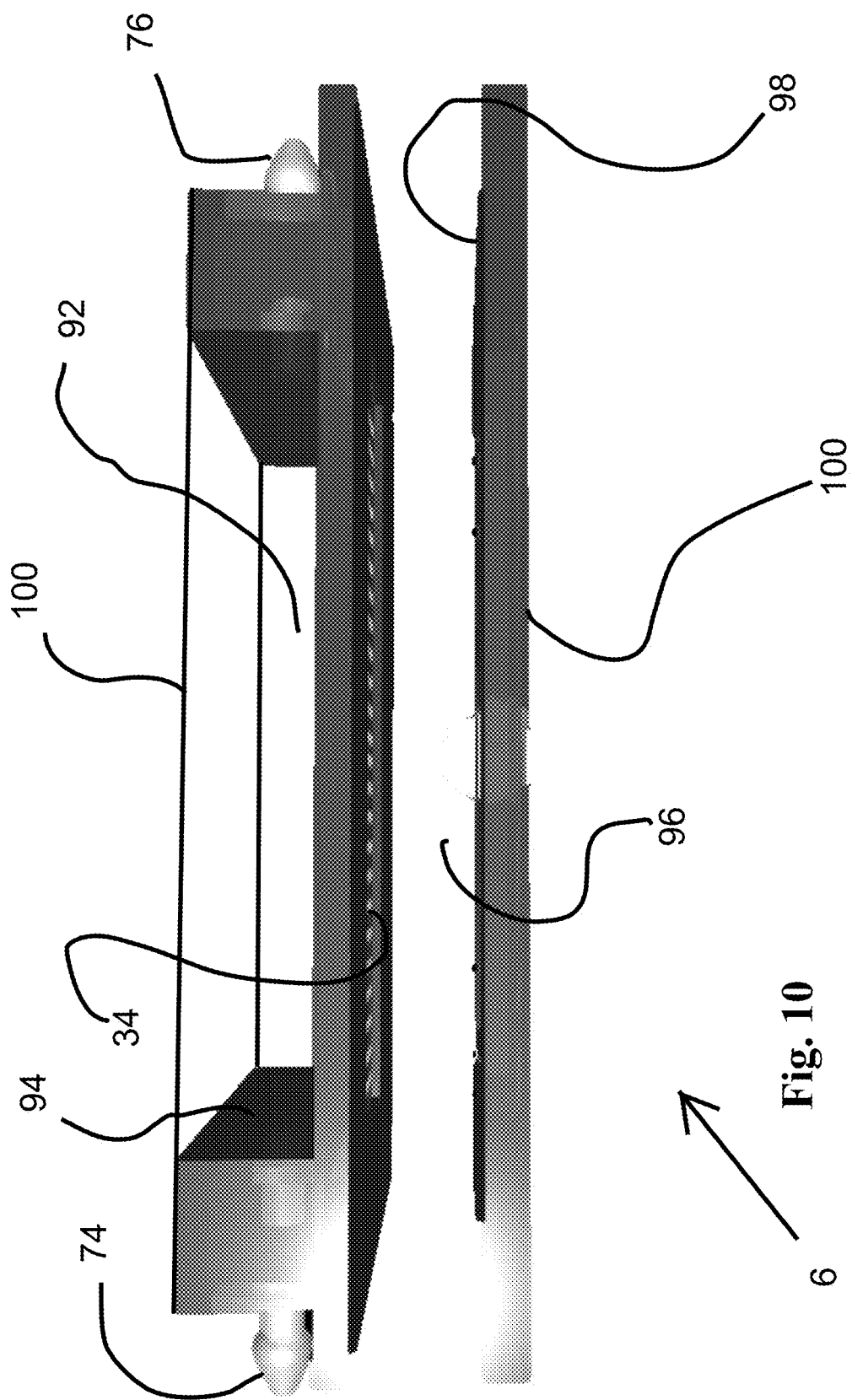
FIGS. 10 and 11 are exploded isomeric views of a second embodiment of the hydraulic cell flexing device with linear elongate cell well/flexing chamber.
Figure 11:
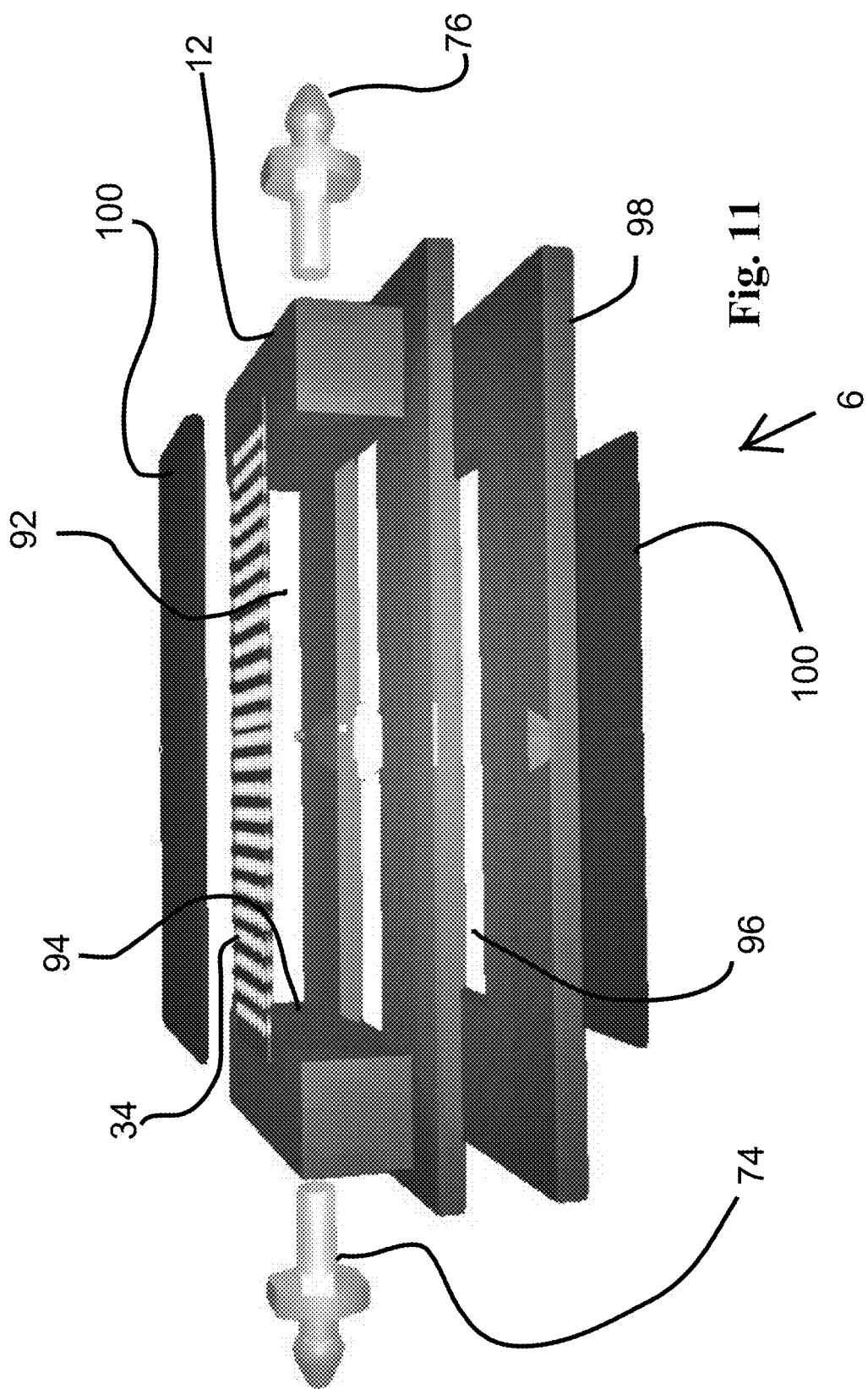

As shown in FIGS. 10 and 11, the baseplate 12 configuration can be further modified to simulate conditions that exist in blood vessels, in which cells are subjected to both cyclic stretch and shear stress due to the flow of fluid 68 across the apical surfaces of the cells (e.g. endothelial cell surfaces). In this case the channels 90 in the baseplate 12 are rectangular and elongate in shape. The flexible membrane 34 is cut to fit within an upper recess 92 in the upper structure 94 of the flexing chamber 6. The flexible membrane 34 (silicone or other flexible material, including tissue specific cell matrix components,) would be preferably either a solid surface or perforated with micropores (between 5-30 μm), the latter membrane 34 could be used in studies requiring co-culture of cells above and below the plane of the silicone membrane 34, with cells below the plane of silicone in a lower recess 96 in the lower structure 98. For single cell culture, cells would be seeded into the upper chamber (the area enclosed by a clear glass cover 100 cemented to the top of the upper structure 94 and the silicon support 35 cemented to the bottom of the upper structure 94) of the flexing chamber 6. The distance between the glass 100 and the silicon 34 would be preferably between 0.1-1 mm. The presence of the upper glass 100 allows for microscopic images of the cells in situ in the upper chamber 94 in the device. A similar configuration with a layer of glass 100 bounding the bottom surface of the lower structure can be put in place in the lower chamber/recess 96 of the flexing chamber 6 to image cells grown on the underside of the perforated material 34.

Input 74 to the baseplate 12 of the flexing chamber 6 would be from the hydraulic drive module 24 (e.g. hybrid linear actuator 20). The output 76 from the opposite side of the baseplate 12 would be regulated by a computer-controlled valve 60 that is capable of opening/closing in a time-dependent fashion. The cycling timing of the valve 60 (i.e. open/close) would be regulated to be closed at the time of the generation of a positive, pulsatile force from the hydraulic drive module 24, opening in a time interval once the pulsatile force from the hydraulic drive module 24 is complete. Synchronization between the actuator 20/hydraulic drive module 24 pulse and the output valve 60 would be regulated via the linear encoder 36 device associated with the hydraulic drive module 24. An offset in synchronization will generate the positive pressure within the baseplate 12 apparatus needed to stretch the flexible membrane 34. Once the pressure cycle is complete, the timed opening of the valve 60 would allow for the flow of the fluid 68 from the flexing chamber 6, the entrance and exit of the fluid 68 from the flexing chamber 6 providing the shear flow component. The output from the valve 60 would be reticulated back to the hydraulic drive system 2. Since this system could potentially be used for longer-term culture purposes, a fluid reservoir 102 for holding tissue culture medium (the hydraulic fluid 68 in this system) and gas exchange circuit would be incorporated into the circuit.

Figure 14:
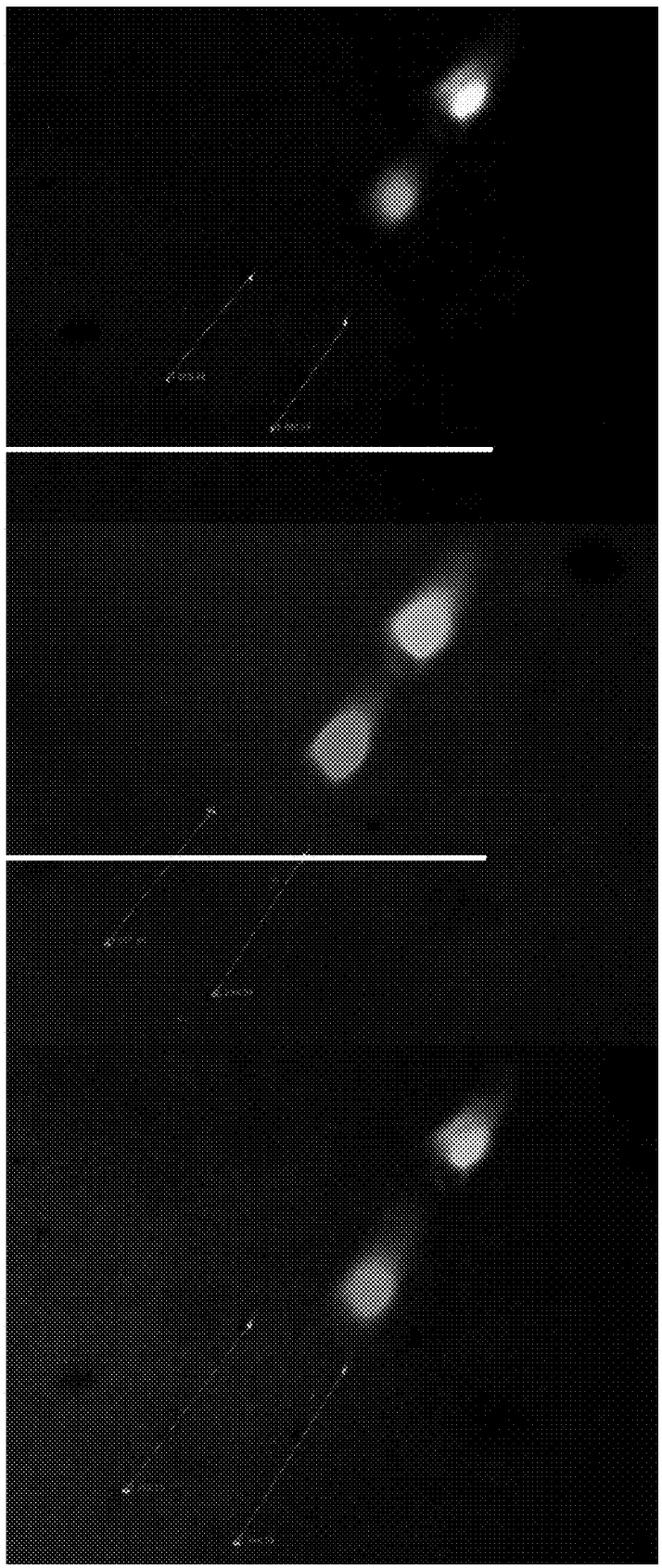
FIG. 14 is a composite of three images of measurements taken with the device of FIG. 1.
Figure 15:
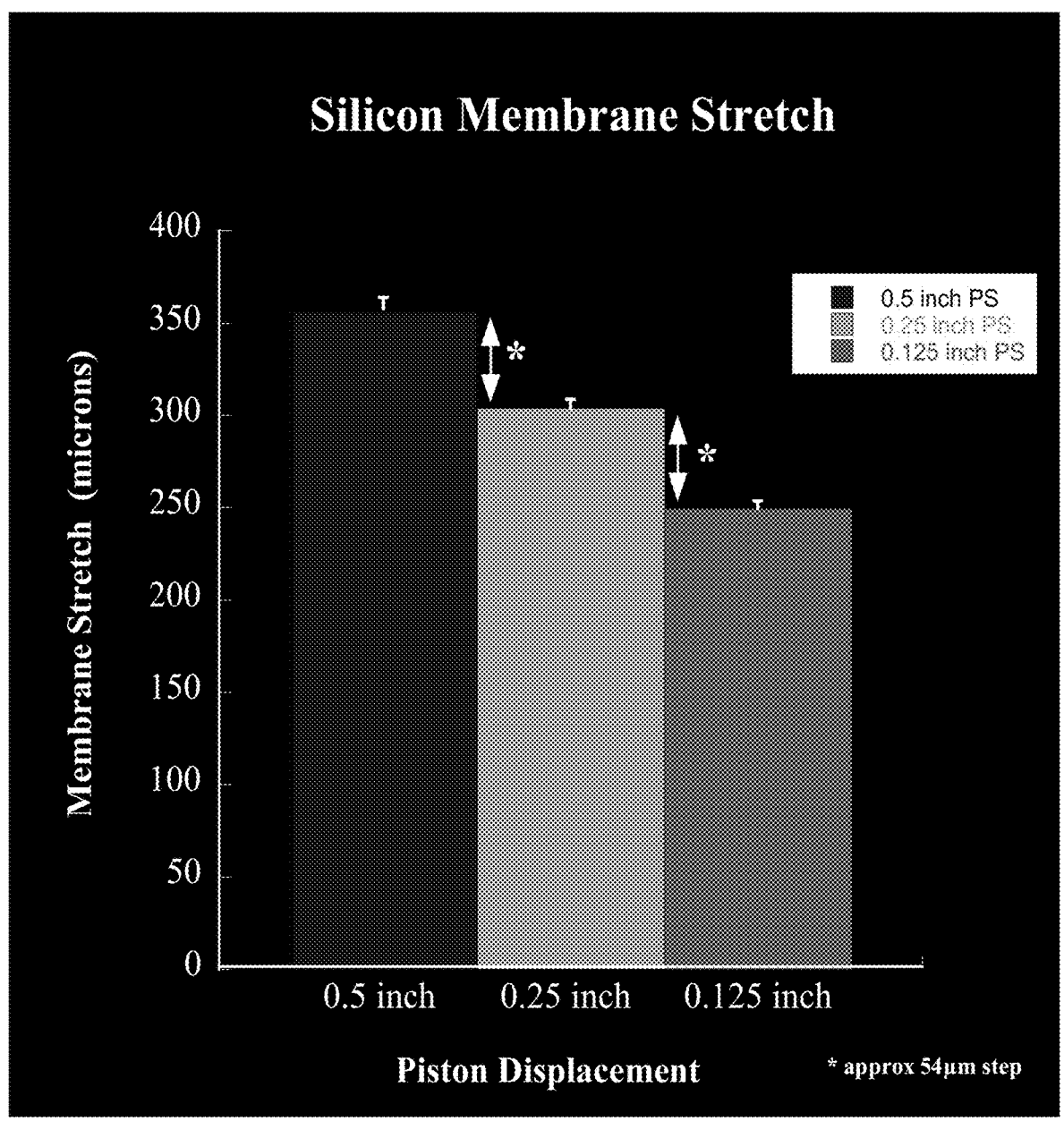
FIG. 15 is a graph of membrane stretch to various lengths of piston stroke of the device of FIG. 1.

Testing—Turning now to FIG. 14, this Figure shows three composite images of measures taken at piston 32 strokes of 0.125" (upper), 0.250" (middle) and 0.5" (lower). The red bars in each panel show the line measures taken between fiduciary fluorescent microspheres which were covalently coupled to the silicon membrane 34. The graph shown in FIG. 15 summarizes the measures taken. Based on the design of the first embodiment, the minimal length of the stretch has been decreased to 15 microns in length, a surprisingly precise level of flex.

Continuing with FIG. 15, measurements with the first embodiment showed that a 0.5" piston 32 stroke resulted in a 350 μm displacement/stretch of the membrane 34; a 0.25" piston 32 stroke resulted in a 303 μm displacement of the membrane 34, and a 0.125" piston 32 stroke resulted in a 249 μm displacement of the membrane 34. The graph of FIG. 15 is a presentation of the data, where 5 trials were conducted, with 10 measures per trial.

Turning next to FIGS. 16 and 17, two embodiments with multiport manifolds 104, 116 upstream and downstream of the well 8 columns are shown. In FIG. 16, the variable hydraulic pressure source 4 is the linear actuator 20/piston cylinder assembly 22 drive module 24. The flow arrows 78 indicate the one way flow of fluid 68 along the fluid circuit 16 starting from a junction point 106, to and then from the wells 8. During a high pressure stroke of the piston 32, fluid 68 leaves the cylinder 44 and continues toward the wells 8 along the fluid delivery path 108 (the upper path in the figure) through a delivery one-way check valve 110. The fluid return path 112 (the lower path in the figure) is blocked by a return one-way check valve 114. The two check valves 110, 114 in the circuit prevent flow from occurring in the wrong direction. After the fluid 68 passes the delivery check valve 110 it comes to the delivery manifold 104. The delivery manifold 104 has a separate computer controlled gate valve 118 for each line 16, which can control the amount of fluid 68, pressure of fluid 68, and the time of fluid delivery for each line 16, for example. It is understood that the gate valve 118 can shut all the way, closing the hydraulic path 16 to a particular column of wells 8, or open all the way, providing substantially no resistance to fluid flow. When fluid 68 is allowed to pass a respective gate, fluid 68 then passes the delivery manifold 104 into its respective column of wells 8. Down stream, and fluidically connected to the wells 8 is a return manifold 116, which has a separate computer controlled gate valve 118 for each line 16, which can control the amount of fluid 68, pressure of fluid 68, and the time of fluid 68 maintained in each line 16, for example. Through the cooperative action of the delivery manifold 104 gate valves 118 and the return manifold 116 gate valves 118, fluid 68 pressure, volume, and velocity are regulated in the different well 8 columns. For example, to build up pressure in a column of wells 8, and thus flex the well membranes 34 and hence the cells, the return manifold 116 gate valves 118 will close and the delivery manifold 104 gate valves 118 will open. For a low pressure in a given column of wells 8, the return manifold 116 gate valve 118 will open, dumping hydraulic fluid 68 to the sump 70 and the delivery manifold 104 gate valve 118 will close, preventing additional hydraulic fluid 68 from entering the wells 8, and thus unflexing the well membranes 34 and hence the cells. The fluid 68 pressure build up and release are preferably coordinated with the piston 32 stroke, opened delivery manifold 104 gate valves 118 and closed return manifold 116 gate valves 118 during the high pressure stroke, and closed delivery manifold 104 gate valves 118 and open return manifold 116 gate valves 118 during the low pressure stroke of the piston 32. It is to be noted though, that with precise enough control of the two manifolds' 104, 116 gate valves 118, and due to the delivery and return one-way check valves 110, 114, the delivery and return manifold 104, 116 gate valves 118 could be opened and closed independent of the piston 32 stroke, so long as sufficient fluid 68 pressure is in the circuit upstream of the delivery manifold 104. That is, the hydraulic circuit between the delivery check valve 110 and the delivery manifold 104 can act as a hydraulic pressure accumulator 120. It is noted that an additional designated pressure accumulator 120 may be placed along the hydraulic circuit upstream of the delivery manifold 104.

Turning to FIG. 17, an embodiment is shown similar to the embodiment in FIG. 16, except that the linear actuator 20/piston cylinder assembly 22 drive module 24 and the delivery and return one way check valves 110, 114 have been replaced by a continuous source of hydraulic pressure, like a hydraulic pump 58. Similar to the embodiment in FIG. 16, the hydraulic line 16 between the hydraulic pump 58 and the delivery manifold 104 can act as a hydraulic pressure accumulator 120, or a designated accumulator may be added to the circuit. The delivery manifold 104 gate valves 118 would open, preferably in a manner based at least partly on the amount of fluid pressure in the upstream line 16, and close, in coordination with the return manifold 116 gate valves 118, to create a similar cyclic flexing of the well membranes 34 as experienced with the linear actuator 20/piston cylinder assembly 22 drive module 24.

Turning next to FIG. 18 an embodiment with multiple actuator 20 drive modules 24 is shown. In the configuration shown, hydraulic force is supplied by the four separate hybrid captive linear 20/piston cylinder assembly 22 drive modules 24. The four drives modules 24 are capable of independent operation. Each drive module 24 is hydraulicly linked via flexible fluidic connection 16 to a column of multiple wells 8 on the baseplate 12, in this instance there are four columns and three wells 8 per column. The fluidic connection 16 depicted is from the drive module 24 to both ends of the column in order to deliver a more even hydraulic force across all wells 8 in the column. However, the fluidic connection 16 could just be made at one location along the column. The flow arrows 78 show the flow of hydraulic fluid 68 as the piston 32 makes a high pressure stroke (away from the linear actuator 20 as depicted in the Figure). The fluidic sensor system 122 provides hydraulic force information and system failure information and is communicated to the computer 38 which controls the system 2. In this configuration, the cells in each column of wells 8 is capable of being flexed individually with regard to rate and degree/extent of cyclic stretch as compared to the cells of other columns of wells 8. The wells 8 in each column are fluidically connected to other wells 8 in the same column. A linear encoder 36 sends information back to the controller 38 with regard to the performance of the system, for example valve open/close, rate, number of valve cycles/unit time. Communication 124 is achieved either via direct/wired connection or via wireless (e.g., WIFI/bluetooth) type of architecture or both.

Figure 19:
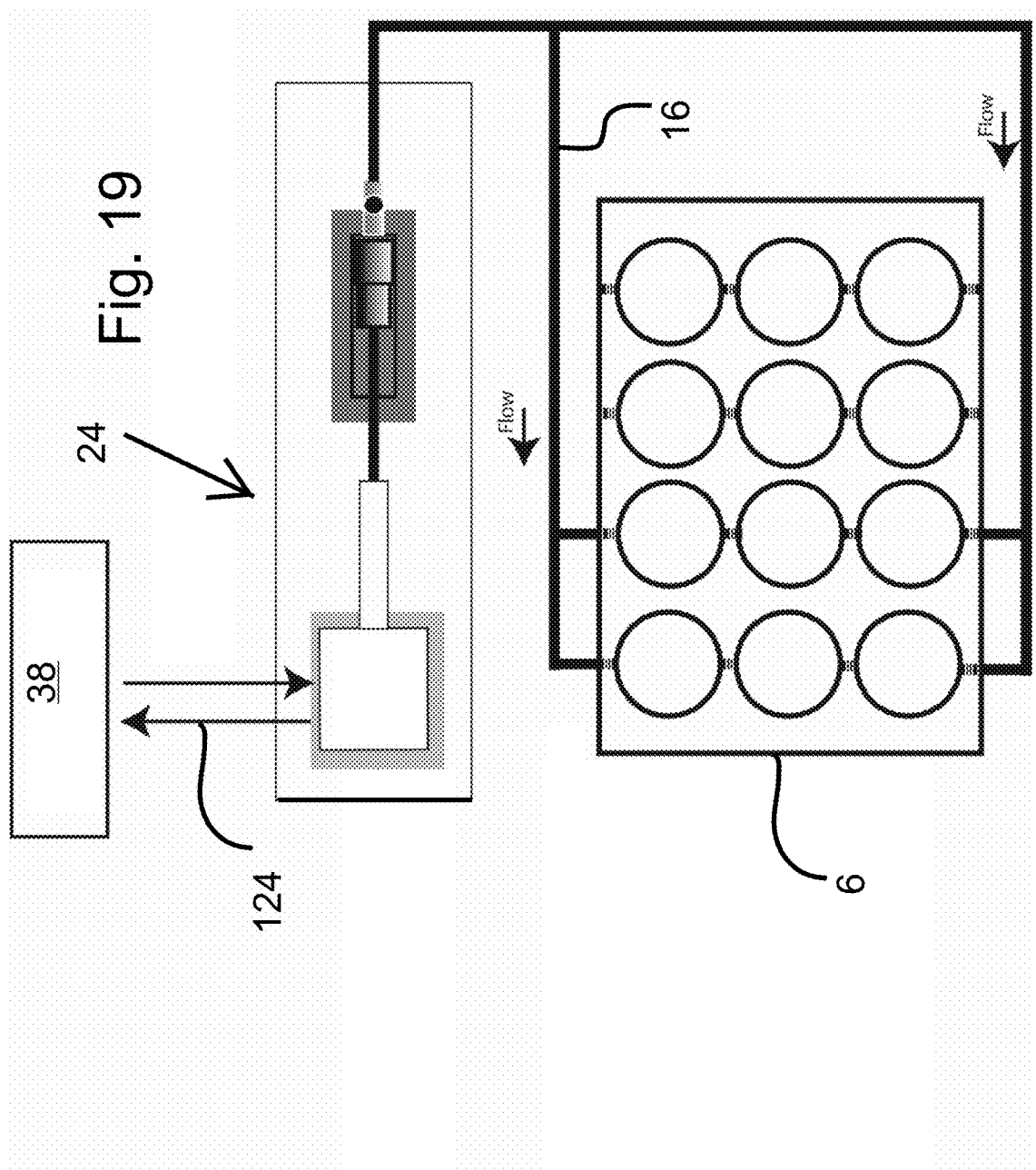
FIG. 19 is a schematic drawing of a hydraulic cell flexing device with a single drive module delivering fluid to a multi-column of wells.

Turning now to FIG. 19, an embodiment with a single drive module 24 delivering fluid 68 to a multi-column of wells 8 is shown. In this configuration, hydraulic force is supplied by the hybrid captive linear actuator 20/piston cylinder assembly 22 drive module 24 and linear encoder 36 system. The actuator 20 is controlled by the computer controller 38 (which could be internal to the actuator) and powered by the power supply 126 (which could also be internal). In the embodiment shown, the power 126 is supplied as DC current. The linear encoder 36 sends information back to the controller 38 with regard to the performance of the system (stroke length, rate, number of strokes per unit time) Each vertical column of, for example, three wells 8 is coupled to actuate as a single functional unit. Each column is linked to the hydraulic fluid path 16 on both sides of the baseplate 12 to ensure equalization of hydraulic pressure within a column. The two uncoupled columns in the Figure represent "control" wells 8, cells that are grown in the same flexing chamber 6 under the same conditions, but where for the particular portion of the flexing chamber 6 no flexing protocol is applied. The flow arrow 78 indicates flow of hydraulic fluid 68 during a high pressure stroke of the piston 32.

Figure 20:
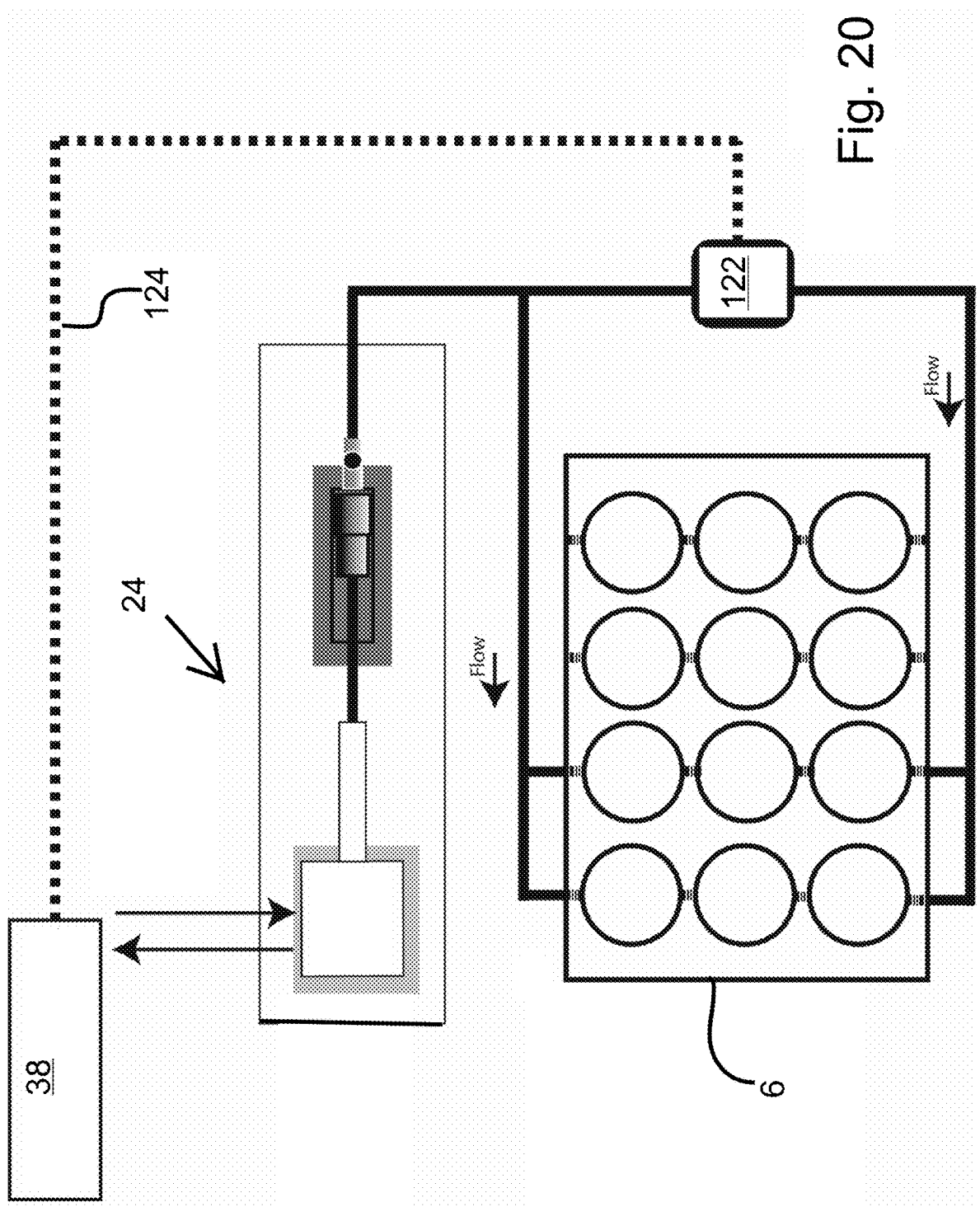
FIG. 20 is a schematic drawing of the hydraulic cell flexing device of FIG. 19 with a fluidic sensor system placed along the hydraulic circuit.

Turning next to FIG. 20, an embodiment similar to FIG. 19 is shown. In this embodiment though, a fluidic sensor system is placed along the hydraulic line 16 between the drive module 24 and the wells 8. The fluidic sensor system 122 preferably communicates with the computer controller 38 either directly or via wireless connection 124. The fluidic sensor system 122 could be independently controllable though. Power 126 into the linear actuator 20 is preferably filtered DC, preferably with an integrated uninterruptible power supply battery backup system to allow many month operation and experimentation (e.g., long term flexed cell growth), regardless of power outages.

Figure 21:
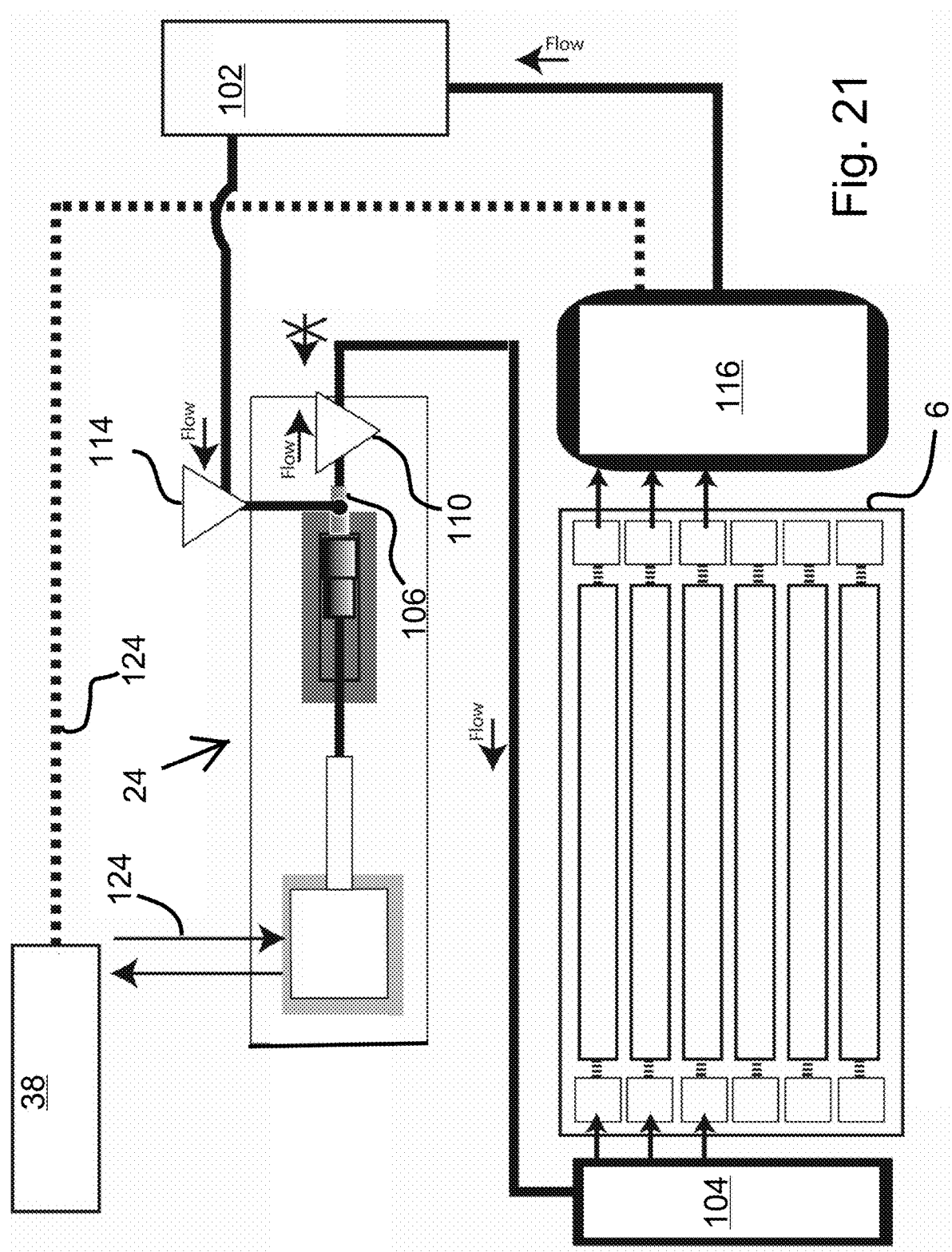
FIG. 21 is a schematic drawing of a hydraulic cell flexing device with a plurality of linear flex plates of FIGS. 10 and 11.

Turning to FIG. 21, a pumping system with a plurality of linear flex plates is shown, similar to the embodiment described in FIGS. 10 and 11. In this embodiment, hydraulic force is supplied by the hybrid linear actuator 20. The linear encoder 36 sends information back to the controller 38 with regard to the performance of the system (stroke length, rate, number of strokes/unit time). Communication 124 between the system and the computer controller 38 is done preferably via direct/wired connection or via wireless (WIFI/bluetooth) type of architecture. The flow arrows 78 indicate the one way flow of fluid 68 along the fluid circuit 16 starting from a junction point 106, to and from the wells 8. During a high pressure stroke of the piston 32, fluid 68 leaves the cylinder 44 and continues toward the wells 8 along the fluid delivery path 108 (the lower pathway in the Figure) through a delivery one-way check valve 110. The fluid return pathway 112 (the upper pathway in the Figure) is blocked by a return one way the circuit 114 prevent flow from occurring in the wrong direction. Fluid 68 then flows into a distribution/delivery manifold 104 and is distributed to one of the plurality of linear wells 8. In the embodiment shown, the baseplate 12 is set up for shear flow flexing through the upper three of the linear wells 8. The remaining lower three control wells 8 are shown unconnected, so as to be held in static conditions as controls. It is conceived that the distribution/delivery manifold 104 could have internal controls, controlled directly or remotely, that would open or close internal gate valves 118, and/or moderate pressure/fluid 68 delivered from the separate fluid lines 16 leaving the distribution/delivery manifold 104. In such an configuration, the three control wells 8 could be fluidly attached to the distribution/delivery manifold 104, but the distribution/delivery manifold 104 would just shut an internal gate valve 118 preventing pressurized fluid 68 or moderations in fluid pressure from being delivered to the control wells 8 for set or open ended periods of time.

Connected to a downstream side of the wells is a multi-chanal valve/return manifold 116, comprising gating valves 118 and fluidic sensor system 122. The fluidic sensor system 122 provides hydraulic force information and system failure information to the computer controller 38. The gating valve 118 regulates the downward force needed to flex the silicone membrane 34 by opening, for example, "out of phase" from the pumping action of the hybrid captive linear actuator 20. The degree of opening and length of time of opening could be varied, including allowing the hydraulic pressure in the wells 8 to reach ambient pressure, or maintaining hydraulic pressure in the wells 8 as above ambient pressure. Fluid 68 then flows from the multi-channel valve/return manifold 116 to a medium reservoir 102 and oxygenation circuit, as described above, where the medium 68 will be conditioned (e.g., through filters and reverse osmosis systems) to add nutrients—including oxygen, and remove waists, and stabilize temperature. Alternatively, fluid 68 from the multi-channel valve/return manifold 116 could be dumped in a sump 70 and new, conditioned fluid 68 could drawn into the system from a fluidically separate holding tank (not shown). Fluid 68 is drawn out of the reservoir 102 and into the system 2 as a result of the piston's 32 low pressure stroke creating a low pressure in the hydraulic line 16. The new/conditioned fluid 68 flows through the return one way check valve 114 and back to the junction point 106.

According to one embodiment, for control wells 8, during the high pressure stroke, both the delivery manifold 104 and the muti-channel valve/return manifold 116 gate valve 118 pathways to the control wells 8 could be open. This would flush fluid 68 through the control wells 8 delivering oxygen, heat/cool, and nutrients and remove wastes, with out significantly increasing pressure or flexing the control wells. This process would preferably occur at the same time in the non-control wells 8 to prevent introducing additional variables into the experiment. The delivery manifold 104 gate valve 118 would then close to the control wells 8, followed by or simultaneous as the muti-channel valve/return manifold 116 gate valves 118 closing to all wells 8. The delivery manifold 104 gate valve 118 for non-control wells 8 would then open (if not opened already), increasing pressure (and hence flex) on the non-control wells 8. Alternatively, control wells 8 could be connected to a separate low flow, low pressure and/or static pressure hydraulic circuit to circulate fluid 68 and deliver nutrients and remove waists to the cells in the control wells 8.

Figure 22:
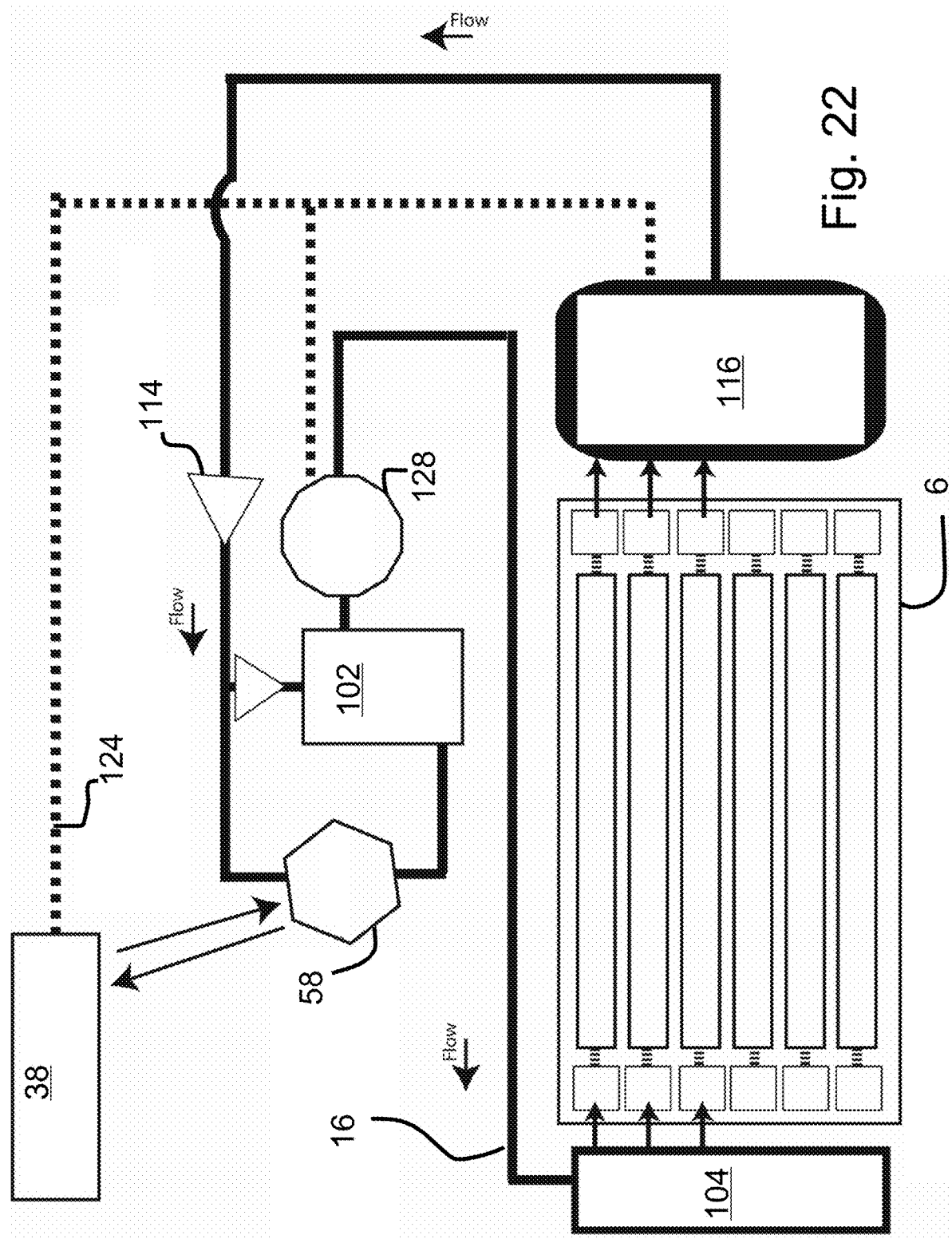
FIG. 22 is a schematic drawing of a hydraulic cell flexing device with a plurality of linear flex plates and a rotary vane pump.

Turning next fo FIG. 22, an embodiment similar to FIG. 21 is shown, but a different hydraulic pump 58 (e.g., a rotary vane pump 58) is used to generate hydraulic pressure and move hydraulic fluid 68. Also, the reservoir 102 is positioned downstream of the pump 58 but upstream of the wells 8. The reservoir 102 could also be positioned upstream of the pump 58, between the pump 58 and the multi-channel valve/return manifold 116. Between the pump 58 and the delivery manifold 104 is a variable rate gating valve 128, which controls the amount of fluid 68 and/or pressure that is transferred down stream. A pressure accumulator 120 may also be positioned between the pump 58 and the variable rate gaiting valve 128.

Figure 23:
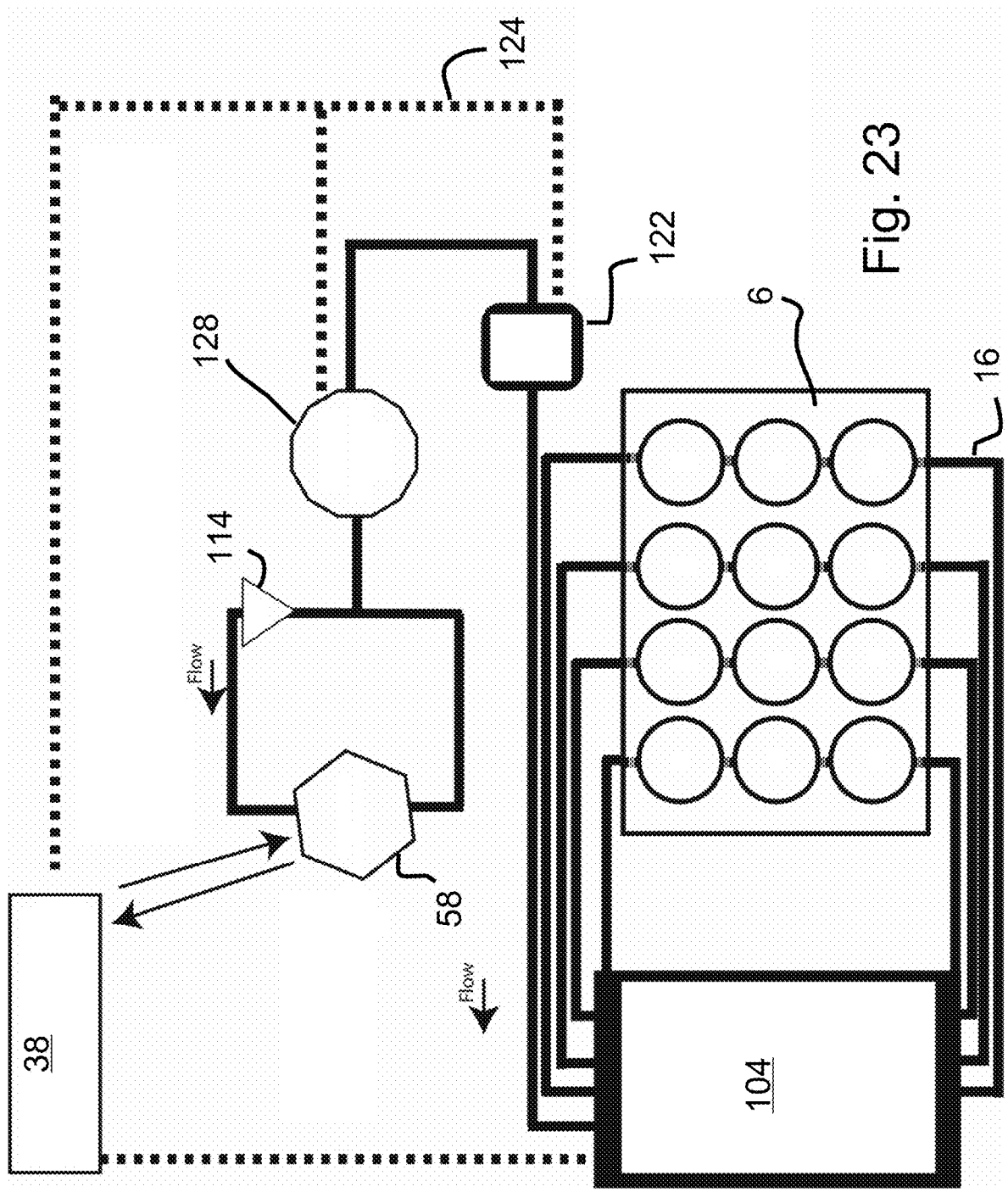
FIG. 23 is a schematic drawing of a hydraulic cell flexing device with a rotary vane pump and manifold with multi-channel hydraulic flow/pressure regulator valves.
Figure 24:
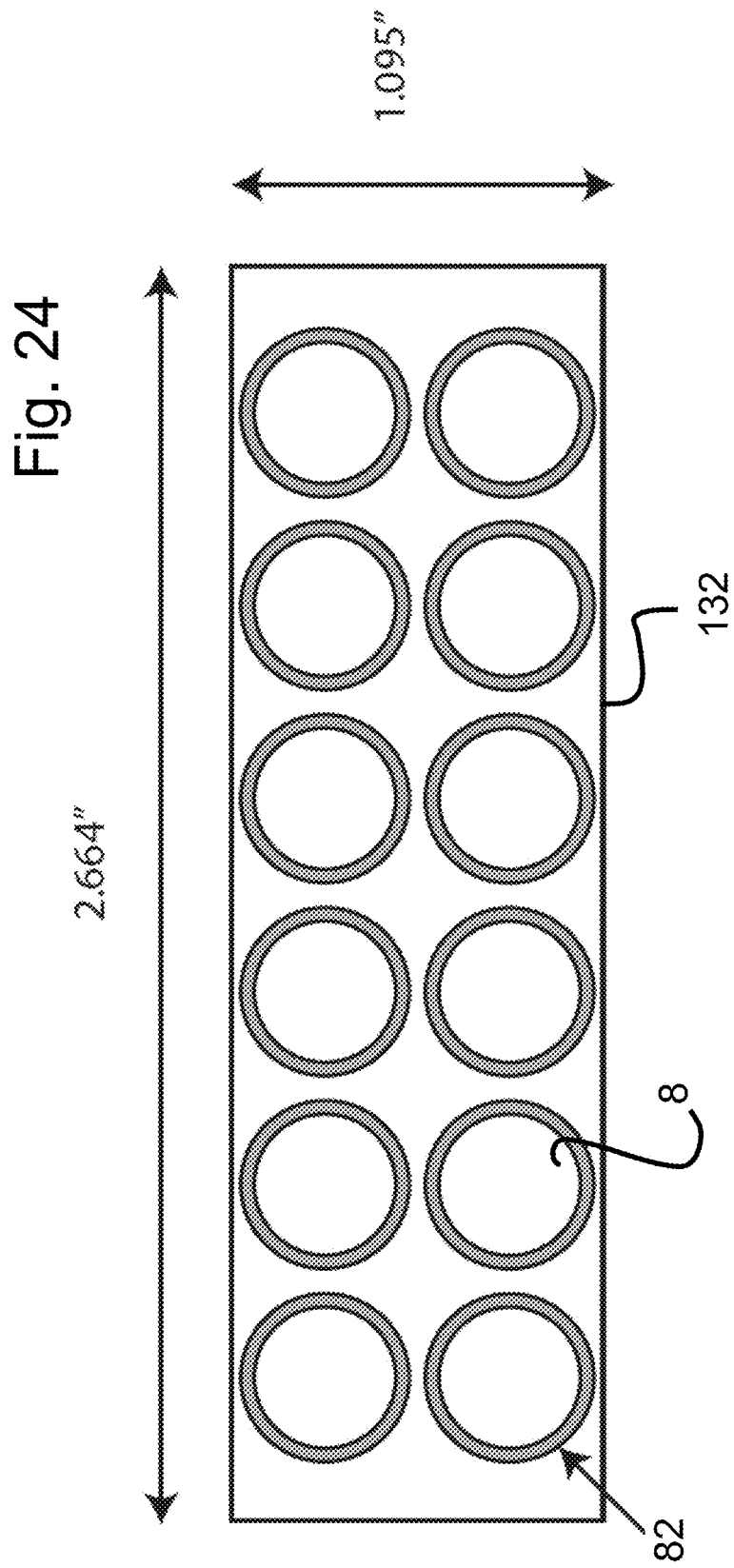
FIG. 24 is a schematic drawing of a bottom view of an upper plate of a microwell plate flexing chamber.
Figure 25:
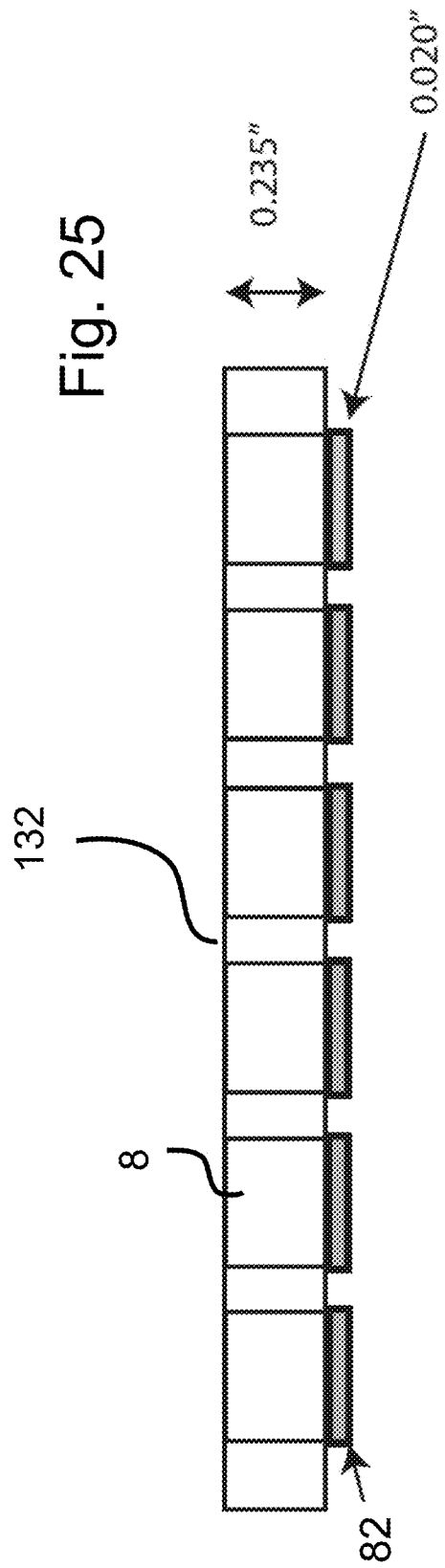
FIG. 25 is a schematic drawing of a side view of the upper plate of the microwell plate flexing chamber of FIG. 24.
Figure 26:
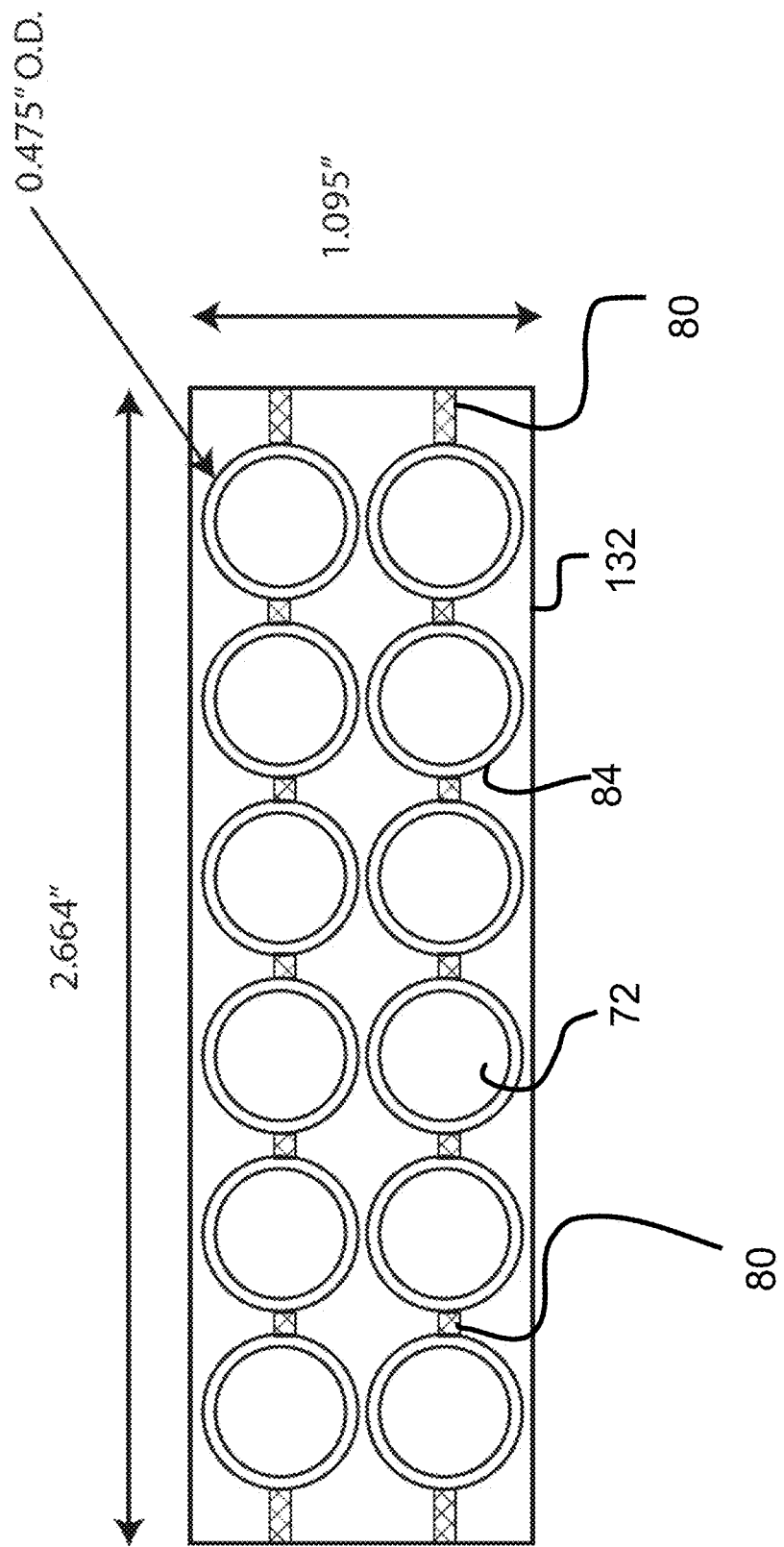
FIG. 26 is a schematic drawing of a top view of a lower plate of a microwell plate flexing chamber.
Figure 27:
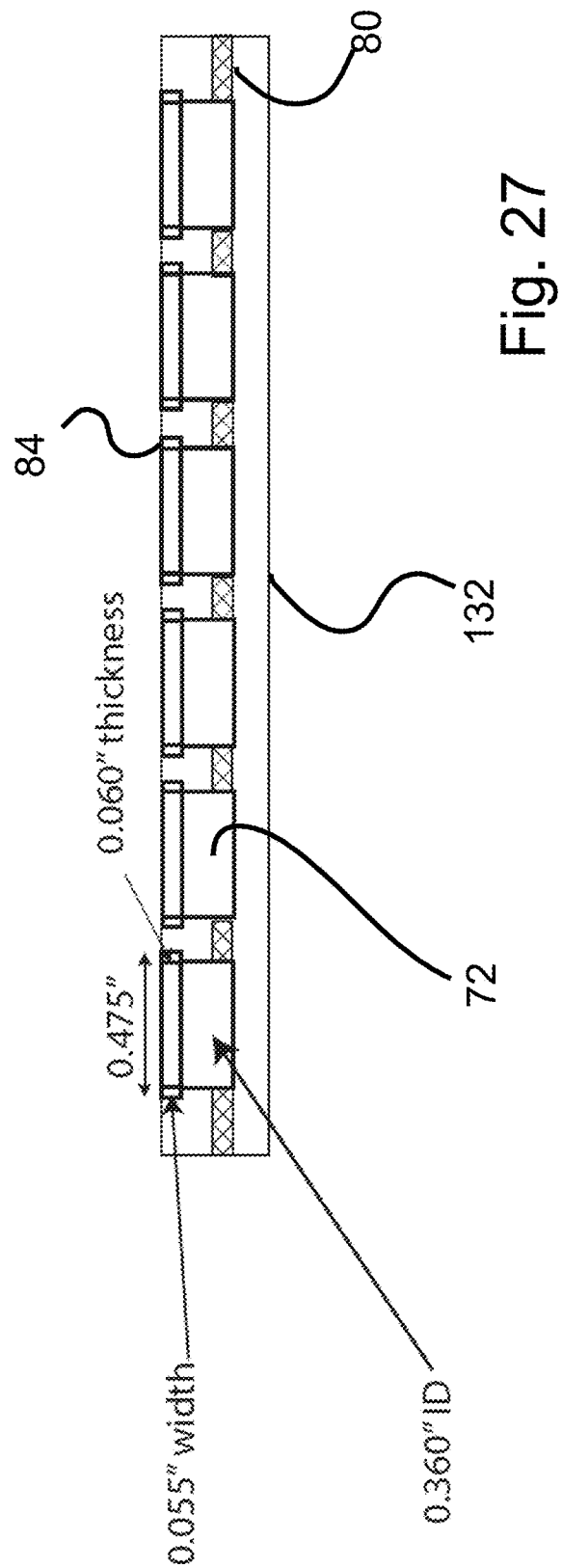
FIG. 27 is a schematic drawing of a side view of the lower plate of the microwell plate flexing chamber of FIG. 26.

Turning next fo FIG. 23, an embodiment using a rotary vane pump 58 as the source of variable pressured hydraulic fluid 4, similar to FIG. 22, is shown. In this embodiment though, the reservoir 102 and a check valve 114 is removed, a fluidic sensor system 122 is placed along the hydraulic line 16, between the delivery manifold 104 and the variable rate gating valve 128, and the cell wells 8 are circular and arranged in columns. The delivery manifold 104 in this embodiment is a multichannel hydraulic flow/pressure regulator valve capable of directing flow/pressure paths to each individual columns of wells 8, permitting simultaneous multiplex flexing within the same plate 12. For example, all of the wells 8 in the farthest left column in the Figure could flex at a different rate/extent from those in, say, the farthest right column in the Figure. The flow/pressure regulator valve would be computer 38 controlled, with either internal computer control components 38 or external by an external computer control 38, or both.

ADDITIONAL EMBODIMENTS—The baseplate 12 configuration can be scaled up in number of wells 8 to dimensions that would incorporate standard cell culture well 8 configurations (including, for example, 6, 12, 24, 96, and 384 wells 8, and well 8 configurations not in multiple of 3, such as n*2 or n*5). Alternatively, each cell well 8 could be separately directly attached to a pressure line. The baseplate 12 can also be "scaled down" in overall size of individual wells 8 using micromachining methods to accommodate a well 8 configuration where the size of each well 8 is capable of holding a single cell for studies that would explore single-cell response systems.

Turning thus to FIGS. 24-28, the figures demonstrate a microwell plate 130 format flexing chamber 6 that facilitates imaging of cell response to stretch using an upright microscope format. The microwell plate 130 consists of an upper plate 132 and lower plate 134, both of which "sandwich" a layer of flexible silicon 34 (1.095"×2.664"; not shown in drawing for clarity). The upper plate 132, silicon layer 34, and lower layer 134 may be permanently cemented together to form a single unit structure 130. As in the larger flexing chamber 6 above, there is a rim of material 82 (extending −0.020" from the surface of the lower face) surrounding each well 8 of the upper plate 132 that interfaces with a groove 84 surrounding each well 8 of the lower plate 134. As with the flexing chambers 6 of other disclosed embodiments, the interaction of the rim 82 with the groove 84 particularly aids in providing a consistent baseline stretch of the silicon membrane 34 during assembly of the complete flexing chamber 6, 130. A channel links a row of cells for the purposes of flexing. Thus each microwell plate 130 shown contains two rows of cell wells, each row being capable of being independently flexed from the other row. What is not shown on the diagram (for the sake of clarity) are the couplers that permit the attachment of the hydraulic lines 16 from the pump 58 unit to each microwell plate 130. Each end of the row would be attached to the same hydraulic line 16 to ensure equal distribution of hydraulic force along the length of the row. An optional addition to the flexing chamber 6 would permit the placement within one well 8 from each row of a pressure/strain or other sensor to provide real-time readout to the host computer 38 of the mechanical strain occurring during the flex cycle for each row.

A further embodiment on the above variations would provide a separate well 8 access or hydraulic port for each well, preferably though the bottom of the baseplate 12 or microwell plate 130. In this way, the experimenter can vary conditions for each of the, for example, 384 wells 8 on a microwell plate 130. An expanded manifold 114, similar to the manifold in FIG. 23, with computer controlled microvalves and pressure gages, could provide for specific pressures, levels, rates, and durations of fluid 68 delivery to and from each well, with separate line or lines 16 to each. For convenience, this modified access further embodiment could comprise a mounting seat with mating (male/female) access ports in the upper face to engage the access ports in the bottom surface of the microwell plate 130. The microwell plate 130 would sit in the mounting seat, and become fluidicly connected. Each mating access port on the mounting seat would be fluidically connected, via a separate internal channel internal to the mounting seat to a lateral exterior port, preferably on a lateral facing surface of the mounting seat. The each lateral exterior port would then have a separate fluid line 16 to the expanded manifold. The separate fluid lines 16 and the mounting seats could be produced together. The separate fluid lines 16 could engage with the expanded manifold via a mating cartridge attachment, providing quick, secure, and releasable connection between the, for example, 384 fluid lines 16 and the, for example, 384 ports on the expanded manifold. If a full circuit was desired for each well, two ports would be provided for each well, and say, 768 lines 16 would be provided for a 384 port multi well 8 plate.

It was observed that different thicknesses of membrane 34 flex to different magnitude in response to a same fluidic force applied. To take advantage of this discovery, an alternative embodiment uses at least two different cell wells 8, for example in the same or different columns, with the two different cell wells 8 having cell well membranes 34 of different thicknesses. This would allow experiments of different cell flexing in different cell wells 8 with a single pressure and amount of fluid 68 delivery.

At face value, the disclosed device 2 could be used for exploring basic research questions with regard to the effects of cyclic stretch of cells (similar to what occurs in vivo in blood vessels). The use of the device 2 could be extended by scaling up, for example, to drive the differentiation of pluripotential stem cells towards a vascular smooth muscle phenotype which could be used in tissue engineering applications (e.g construction of engineered blood vessels) or the production of cell-type specific extracellular matrices. Previous work (unpublished) in the laboratory has shown that bone marrow-derived stem cells could be differentiated towards a smooth muscle cell phenotype by prolonged cyclic stretch. For this type of application, bone marrow-derived stem cells would be seeded into the cell wells 8 of a flexing baseplate 12 and then subjected to cyclic stretch (approximately 4 Hz) for a period of a week. Previous (unpublished) studies in the laboratory showed that the stem cells would take on a smooth muscle phenotype over that time period. The cells could be directly harvested from the device 2 using standard cell culture methods and used in downstream tissue engineering applications. The differentiation process can be accelerated via the introduction of several known growth factors during the flexing regimen.

The accuracy of the disclosed device 2 allows a more close representation of the true stretch environment experienced by some cells in vivo during a cardiac cycle. This includes not only a flex and relaxation cycle, but a stretch, partial relaxation, partial stretch, relaxation cycle "hydraulic cardiac cycle"—mirroring the arterial pressure changes of a cardiac cycle: the systolic crest, the incisure or dicrotic notch, and diastolic crest, down to the isovolumetric contraction. The first systolic shoulder can also be represented in a hydraulic cardiac cycle, as can the various overlapping of the ejected wave front and the reflected wave front based on different variable. Additionally, the accuracy of the device 2 allows the experimenter to subject cells to pressure waveforms typical to different parts of a body, for example, aortic, subclavian, axillary, brachial, radial, and femora. Further, the device 2 can readily replicate pressure waveforms typical of different aged individuals, and individuals of differing degree of that and in between the two.

While various embodiments of the present invention have been described in detail, it is apparent that various modifications and alterations of those embodiments will occur to and be readily apparent to those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having," and variations thereof herein, is meant to encompass the items listed thereafter and equivalents thereof as well 8 as additional items while only the terms "consisting of" and "consisting only of" are to be construed in a limitative sense. In addition, the device 2 can emulate the unique pulsatile flow that is found in microvascular beds, such as the capillaries of the renal glomerulus.

We claim:

1. A hydraulic cell stretching device comprising:
   a source of variable pressured hydraulic fluid hydraulically coupled to a flexing chamber;
   the flexing chamber having at least one cell well;
   the at least one cell well having a membrane subjected to the variable pressured hydraulic fluid, wherein the membrane carries a cell culture to be subjected to cell stretching;
   each cell well having multiple hydraulic openings to allow hydraulic fluid into or out of each of the at least one cell well;
   a hydraulic circuit including a fluid delivery path leading to the at least one cell well and a separate fluid return path leading from the at least one cell well;
   one of a one-way check valve and a gate valve positioned along the fluid delivery path;
   one of another one-way check valve and another gate valve positioned along the fluid return path;
   wherein a plurality of cell wells are positioned in a single baseplate;
   wherein a first column of the plurality of wells are fluidically connected to one another and experience a first hydraulic pressure from a first independently operated drive module; and
   wherein a second column of the plurality of cell wells are fluidically connected to one another but are fluidically separate from the cell wells of the first column and wherein the second column of the plurality of cell wells simultaneously experience a second hydraulic pressure from a second independently operated drive module distinct from the first independently operated drive module at the same time as the first column of the plurality of cell wells experiences the first hydraulic pressure.

2. The device of claim 1 wherein the source of source of variable pressured hydraulic fluid includes a linear actuator coupled to a piston and cylinder assembly.

3. The device of claim 2 wherein the linear actuator is an electro-mechanical actuator powered by a stepper motor.

4. The device of claim 3 wherein the stepper motor allows fine gradations of linear travel of an actuator rod per step such that the membrane may repeatablely flex at a maximum length of 15 microns.

5. The device of claim 3 further comprising a linear encoder.

6. The device of claim 5 wherein the linear encoder includes a sensor, transducer or readhead paired with a scale that encodes position and provides feedback to a computer controller with regard to precise positioning of one of the actuator rod, the length of piston strokes, the speed of piston strokes and the number of piston strokes per minute.

7. The device of claim 1 wherein the at least one cell well is over 300 cell wells positioned on a single baseplate.

8. The device of claim 1 further comprising a fluidic sensor system arranged along the hydraulic circuit.

9. The device of claim 1 further comprising a plurality of cell wells and one of a delivery manifold distributing hydraulic fluid among the plurality of cell wells and a receiving manifold receiving hydraulic fluid from the plurality of cell wells.

10. The device of claim 1 further comprising at least one one-way check valve along the hydraulic circuit between the source of hydraulic fluid and the at least one cell well.

11. The device of claim 1 further comprising at least one gate valve along the hydraulic circuit between the source of hydraulic fluid and the at least one cell well.

12. The device of claim 1 further comprising a pressure accumulator along the hydraulic circuit between the source of hydraulic fluid and the at least one cell well.

13. The device of claim 1 wherein the flexing chamber includes a first portion that provides a pathway to hydraulic fluid, a second portion that defines the cell well, and the membrane being sandwiched between the first portion and the second portion.

14. The device of claim 13 wherein the first portion has a mounting point recess, the second portion has a mating inset, and the membrane is captively retained between the first portion and the second portion when the inset is brought to mate with the mounting point recess.

15. The device of claim 1 wherein the flexing chamber comprises a single baseplate, the baseplate defining a hydraulic bore within to direct hydraulic fluid to a plurality of cell wells mounted on the baseplate, the baseplate having a hydraulic inlet to receive hydraulic fluid to the hydraulic bore and a hydraulic outlet to discharge hydraulic fluid from the hydraulic bore.

16. A hydraulic cell stretching device comprising:
a source of variable pressured hydraulic fluid hydraulically coupled to a flexing chamber;
the flexing chamber having at least one cell well;
the at least one cell well being elongate, having a length more than two times a width;
the at least one cell well having a membrane subjected to the variable pressured hydraulic fluid such that the membrane carries a cell culture to be subjected to cell stretching;
a hydraulic circuit including a fluid delivery path leading to the at least, one cell well and a separate fluid return path leading from the at least one cell well
one of a one-way check valve and a gate valve positioned along the fluid delivery path;
one of another one-way check valve and another gate valve positioned along the fluid return path;
wherein a plurality of cell wells are positioned in a single baseplate;
wherein a first column of the plurality of cell wells are fluidically connected to one another and experience a first hydraulic pressure from a first independently operated drive module; and
wherein a second column of the plurality of cell wells are fluidically connected to one another but are fluidically separate from the cell wells of the first column and wherein the second column of the plurality of cell wells simultaneously experience a second hydraulic pressure from a second independently operated drive module distinct from the first independently operated drive module at the same time as the first column of the plurality of cell wells experiences the first hydraulic pressure.

17. A fluidic cell stretching device comprising:
a source of variable pressured fluid, fluidically coupled to a flexing chamber;
the flexing chamber having at least one cell well;
each at least one cell well having a fluid input and fluid output that are vertically aligned with one another,
the each at least one cell well having a membrane subjected to the variable pressured fluid, wherein the membrane carries a cell culture to be subjected to cell stretching;
a hydraulic circuit including a fluid delivery path leading to the fluid input and a separate fluid return path leading from the fluid output;
one of a one-way check valve and a gate valve positioned along the fluid delivery path; and
one of another one-way check valve and another gate valve positioned along the fluid return path;
wherein a plurality of cell wells are positioned in a single baseplate;
wherein a first column of the plurality of cell wells are fluidically connected to one another and experience a first hydraulic pressure from a first independently operated drive module; and
wherein a second column of the plurality of cell wells are fluidically connected to one another but are fluidically separate from the cell wells of the first column and wherein the second column of the plurality of cell wells simultaneously experience a second hydraulic pressure from a second independently operated drive module distinct from the first independently operated drive module at the same time as the first column of the plurality of cell wells experiences the first hydraulic pressure.

* * * * *